(12) United States Patent
Bolli et al.

(10) Patent No.: US 8,133,910 B2
(45) Date of Patent: Mar. 13, 2012

(54) THIOPHENE DERIVATIVES AS S1P1/EDGE1 RECEPTOR AGONISTS

(75) Inventors: Martin Bolli, Allschwil (CH); David Lehmann, Galmiz (CH); Boris Mathys, Pratteln (CH); Claus Mueller, Weil am Rhein (DE); Oliver Nayler, Arlesheim (CH); Beat Steiner, Dornach (CH); Jörg Velker, Huningue (FR)

(73) Assignee: Actelion Pharmaceuticals Ltd., Allschwil (CH)

( * ) Notice: Subject to any disclaimer, the term of this patent is extended or adjusted under 35 U.S.C. 154(b) by 23 days.

(21) Appl. No.: 12/310,762

(22) PCT Filed: Jul. 10, 2007

(86) PCT No.: PCT/IB2007/052742
§ 371 (c)(1),
(2), (4) Date: Oct. 30, 2009

(87) PCT Pub. No.: WO2008/029306
PCT Pub. Date: Mar. 13, 2008

(65) Prior Publication Data
US 2010/0048648 A1    Feb. 25, 2010

(30) Foreign Application Priority Data
Sep. 7, 2006 (WO) .................. PCT/IB2006/053150

(51) Int. Cl.
*A61K 31/4245* (2006.01)
*A61K 31/381* (2006.01)
*C07D 271/06* (2006.01)
*C07D 333/22* (2006.01)

(52) U.S. Cl. ........... 514/364; 514/448; 548/131; 549/70
(58) Field of Classification Search .................. 514/364, 514/448; 548/131; 549/70
See application file for complete search history.

(56) References Cited

U.S. PATENT DOCUMENTS

| | | |
|---|---|---|
| 2004/0058894 A1 | 3/2004 | Doherty et al. |
| 2007/0043014 A1 | 2/2007 | Doherty et al. |
| 2008/0064740 A1 | 3/2008 | Bolli et al. |
| 2008/0176926 A1 | 7/2008 | Bolli et al. |
| 2008/0194670 A1 | 8/2008 | Bolli et al. |
| 2008/0300294 A1 | 12/2008 | Bolli et al. |
| 2008/0318955 A1 | 12/2008 | Bolli et al. |
| 2009/0005421 A1 | 1/2009 | Bolli et al. |
| 2010/0075946 A1 | 3/2010 | Bolli et al. |
| 2010/0240717 A1 | 9/2010 | Bolli et al. |
| 2010/0261702 A1 | 10/2010 | Bolli et al. |

FOREIGN PATENT DOCUMENTS

| | | |
|---|---|---|
| EP | 0 476 646 A1 | 3/1992 |
| EP | 1873153 | 1/2008 |
| JP | 2008120794 | 5/2008 |
| WO | WO-91/15583 A1 | 10/1991 |
| WO | WO-99/46277 A1 | 9/1999 |
| WO | WO-03/062248 A2 | 7/2003 |
| WO | WO-03/062252 | 7/2003 |
| WO | WO 03/105771 | 12/2003 |
| WO | WO-2004/035538 A1 | 4/2004 |
| WO | WO-2004/103279 A2 | 12/2004 |
| WO | WO-2005/014525 A2 | 2/2005 |
| WO | WO-2005/032465 A2 | 4/2005 |
| WO | WO-2005/058848 A1 | 6/2005 |
| WO | WO-2006/010544 A2 | 2/2006 |
| WO | WO-2006/047195 | 5/2006 |
| WO | WO-2006/100631 A1 | 9/2006 |
| WO | WO-2006/100633 A1 | 9/2006 |
| WO | WO-2006/100635 A2 | 9/2006 |
| WO | WO-2006/114400 A1 | 11/2006 |
| WO | WO 2006/115188 | 11/2006 |
| WO | WO-2006/131336 A1 | 12/2006 |
| WO | WO-2006/137019 A1 | 12/2006 |
| WO | WO-2007/001973 A1 | 1/2007 |
| WO | WO-2007/060626 A1 | 5/2007 |
| WO | WO-2007/080542 A1 | 7/2007 |
| WO | WO-2007/085451 A2 | 8/2007 |
| WO | WO 2007/098474 | 8/2007 |
| WO | WO-2007/098474 | 8/2007 |
| WO | WO-2008/076356 A1 | 6/2008 |
| WO | WO-2008/091967 A1 | 7/2008 |

OTHER PUBLICATIONS

Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Alvernhe, G., et al. "Synthesis and reactivity of 3-chlloro-3-trifluoromethylacroleins: stabilization of the tetrahedral intermediate in a nucleophilic vinylic "substitution."" Bull. Soc. Chim. Fr. 131 (1994) 167-172.
Brain, C.T., et al. "Novel procedure for the synthesis of 1,3,4-oxadiazoles from 1,2-diacylhydrazines using polymer-supported Burgess reagent under microwave conditions." Tetrahedron Lett. 40(1999) pp. 3275-3278.
Chakraborti, A.K., et al. "One-Pot Synthesis of Nitriles from Aldehydes Under Microwave Irradiation: Influence of the Medium and Mode of Microwave Irradiation on Product Formation." Tetrahedron. vol. 55 (1999). 13265-13268.
Cui, J., et al. "Design and Synthesis of Highly Constrained Factor Xa Inhibitors: Amidine-Substituted Bis(benzoyl)[1,3]-diazepan-2 ones and Bis(benzylidene)-bis(gem-bimethyl)cycloketones." Bioorganic & Medicinal Chemistry 11 (2003) 3379-3392.
Ecke, G.G., et al. "ortho-Alkylation of Aromatic Amines." J. Org. Chem. 22 (1957) 639-642.
Fürstner, et al. "Iron Catalyzed cross-coupling Reactions." J. Am. Chem. Soc., 124 (2002) 13856-13863.
Gangloff, A.R., et al. "Synthesis of 3,5-disubstituted-1,2,4-oxadiazoles using tetrabutylammonium fluoride as a mild and efficient catalyst." Tetrahedron Letters 42 (2001) 1441-1443.

(Continued)

Primary Examiner — Kamal Saeed
Assistant Examiner — Kristin Bianchi
(74) Attorney, Agent, or Firm — Hoxie & Associates LLC

(57) ABSTRACT

The invention relates to novel thiophene derivatives, their preparation and their use as pharmaceutically active compounds. Said compounds particularly act as immunomodulating agents.

21 Claims, No Drawings

OTHER PUBLICATIONS

Garcia, M.A., et al. "Synthesis, Biological Evaluation, and Three-Dimensional Quantitative Structure—Activity Relationship Study of Small-Molecule Positive Modulators of Adrenomedullin." J. Med. Chem. 48 (2005) 4068-4075.

Gibson, Mark, Editor. Pharmaceutical Preformulation and Formulation. HIS Health Group, Englewood, CO, USA 2001.

Gould, P.L. "Salt Selection for Basic Drugs." Int. J. Pharm. (1986). vol. 33. 201-217.

Greene, T.W., et al. Protective Groups in Organic Synthesis. $3^{rd}$ edition. Wiley. New York, 1991.

Gronowitz, S., et al. "On the Syntheses of Branched Saturated Fatty Acids." Lipids. vol. 28 (1993) 889-897.

Hamze, A., et al. "Synthesis of Various 3-Substituted 1,2,4-Oxadiazole Containing Chiral β- and ⊕-Amino Acids from Fmoc-Protected Aspartic Acid." J. Org. Chem. 68 (2003) 7316-7321.

Hla, T. et al. "An Abundant Transcript Induced in Differentiating Human Endothelial Cells Encodes a Polypeptide with Structural Similarities to G-protein-coupled Receptors." J. Biol Chem. 265 (1990), 9308-9313.

John, E.O. et al. "Reactions of (Difluoroamino)difluoroacetonitrile and (Difluoroamino) difluoroacetamidoxime." Inorganic Chemistry. vol. 27 (1988), 3100-3104.

Kaboudin, K. et al. "One-pot Synthesis of 1,2,4-Oxadiazoles Mediated by Microwave Irrafiation Under Solvent-Free Condition." Heterocycles. vol. 60, No. 10, (2003), 2287-2292.

Kerins, F., et al. "Generation of Substituted Styrenes via Suzuki Cross-Coupling of Aryl Halides with 2,4,6-Trivinylcyclotriboroxane." J. Org. Chem., 67 (2002), 4968-4971.

Khlestkin, V.K., et al. "Recent Advance in the Application of A, O-dialkylhydroxylamines in Organic Chemistry." Current Organic Chemistry. 7 (2003), 967-993.

Kiryanov, A.A. et al. "Synthesis of 2-Alkoxy-Substituted Thiophenes, 1,3-Thiazoles, and Related S-Heterocycles via Lawesson's Reagent-Mediated Cyclization under Microwave Irradiation: Applications for Liquid Crystal Synthesis." J. Org. Chem. 66 (2001) 7925-7929.

Knight, D.W., et al. "Generation and Synthetic Utility of Dianions Derived from Thiophencarboxylic Acids." J. Chem. Soc. Perkin Trans. 1 (1983) 791-794.

Kocienski, P.J. Protecting Groups. Thieme Stuttgart, 1994.

Lamattina, J.L. "The Synthesis of 2-Amino-4-(4-imidazolyl)pyridines." J. Heterocyclic Chem. 20 (1983) 533-538.

Mentzel, M. et al. "N-Methoxy N-methyl amides (Weinred amides) in Modern Organic Synthesis." Journal für praktische Chemie Chemiker-Zeitung. 339 (1997), 517-524.

Meyer, E. et al. "Synthesis of New 1,2,4- and 1,3,4-Oxadiazole Derivatives." Synthesis. (2003), No. 6, pp. 899-905.

Pesson, M., et al. "Antibactériens de synthese—Dérivés de l'acide pipémidique." Eur. J. Med. Chem.15 (1980) 263-268.

Poulain, R.F. et al. "Parallel synthesis of 1,2,4-oxadiazoles from carboxylic acids using an improved, uronium-based, activation." Tetrahedron Letters 42 (2001) 1495-1498.

Remington. The Science and Practice of Pharmacy. $20^{th}$ Edition, Philadelphia College of Pharmacy and Science. 2001.

Sato, N. et al. "Synthesis and evaluation of substituted 4-alkoxy-2-aminopyridines as novel neuropeptide Y1 receptor antagonists." Bioorganic & Medicinal Chemistry Letters 14 (2004) 1761-1764.

Singh, J., et al. "The Growing Synthetic Utility of Weinreb's Amide." Journal für Praktische Chemie. Weinheim, Germany. 342 (2000) 340-347.

Srivastava, R.M. et al. "Synthesis of 3-aryl-5-[thien-3-yl methyl]-1,2,4-oxadiazoles." Synthetic Communications. vol. 29 (1999), 1437-1450.

Suzuki, T. et al. "Synthesis of the Selective 5-Hydroxytryptamine 4 (5-HT) Receptor Agonist (+)-(S)-2-Chloro-5-methoxy-4-[5-(2-piperidylmethyl)-1,2,4-oxadiazol-3-yl]aniline." Chem. Pharm. Bull. 47 (1999), 120-122.

Trapani, G. et al. "Propofol Analogues. Synthesis, Relationships between Structure and Affinity at GABAA Receptor in Rat Brain, and Differential Electrophysiological Profile at Recombinant Human GABAA Receptors." J. Med. Chem. (1998), 41, 1846-1854.

Tsukerman, S.V. et al. "Basicity and structure of .alpha., .beta.—unsaturated ketones of a heterocyclic series. VII. Methyl-substituted analogs of chalcones." Chemical Abstracts Service, XP002467039, STN Database Accession No. 1971: 87024.

Xu, B. et al. "Acyclic Analogues of Adenosine Bisphosphates as P2Y Receptor Antagonists: Phosphate Substitution Leads to Multiple Pathways of Inhibition of Platelet Aggregation." J. Med. Chem. 2002, 45, 5694-5709.

Yan et al. "Discovery of 3-arylpropionic acids as potent agonists of sphingosine-1-phosphate receptor-1 (S1P1) with high selectivity against all other known S1P receptor subtypes." Bioorganic & Medicinal Chemistry Letters. Oxford, GB. vol. 16 No. 14 (2006) 3679-3683.

* cited by examiner

THIOPHENE DERIVATIVES AS S1P1/EDGE1 RECEPTOR AGONISTS

CROSS REFERENCE TO RELATED APPLICATIONS

This application is a United States National Stage Application under 35 U.S.C. 371 of PCT/IB2007/052742 filed on Jul. 10, 2007, which claims the benefit of PCT/IB2006/053150 filed on Sep. 7, 2006, the contents of each of which are incorporated herein by reference in their entirety.

FIELD OF THE INVENTION

The present invention relates to S1P1/EDG1 receptor agonists of Formula (I) and their use as active ingredients in the preparation of pharmaceutical compositions. The invention also concerns related aspects including processes for the preparation of the compounds, pharmaceutical compositions containing a compound of the Formula (I), and their use as compounds improving vascular function and as immunomodulating agents, either alone or in combination with other active compounds or therapies.

BACKGROUND OF THE INVENTION

The human immune system is designed to defend the body against foreign micro-organisms and substances that cause infection or disease. Complex regulatory mechanisms ensure that the immune response is targeted against the intruding substance or organism and not against the host. In some cases, these control mechanisms are unregulated and autoimmune responses can develop. A consequence of the uncontrolled inflammatory response is severe organ, cell, tissue or joint damage. With current treatment, the whole immune system is usually suppressed and the body's ability to react to infections is also severely compromised. Typical drugs in this class include azathioprine, chlorambucil, cyclophosphamide, cyclosporin, or methotrexate. Corticosteroids which reduce inflammation and suppress the immune response, may cause side effects when used in long term treatment. Nonsteroidal anti-inflammatory drugs (NSAIDs) can reduce pain and inflammation, however, they exhibit considerable side effects. Alternative treatments include agents that activate or block cytokine signaling.

Orally active compounds with immunomodulating properties, without compromising immune responses and with reduced side effects would significantly improve current treatments of uncontrolled inflammatory disease.

In the field of organ transplantation the host immune response must be suppressed to prevent organ rejection. Organ transplant recipients can experience some rejection even when they are taking immunosuppressive drugs. Rejection occurs most frequently in the first few weeks after transplantation, but rejection episodes can also happen months or even years after transplantation. Combinations of up to three or four medications are commonly used to give maximum protection against rejection while minimizing side effects. Current standard drugs used to treat the rejection of transplanted organs interfere with discrete intracellular pathways in the activation of T-type or B-type white blood cells. Examples of such drugs are cyclosporin, daclizumab, basiliximab, everolimus, or FK506, which interfere with cytokine release or signaling; azathioprine or leflunomide, which inhibit nucleotide synthesis; or 15-deoxyspergualin, an inhibitor of leukocyte differentiation.

The beneficial effects of broad immunosuppressive therapies relate to their effects; however, the generalized immunosuppression which these drugs produce diminishes the immune system's defense against infection and malignancies. Furthermore, standard immunosuppressive drugs are often used at high dosages and can cause or accelerate organ damage.

DESCRIPTION OF THE INVENTION

The present invention provides novel compounds of Formula (I) that are agonists for the G protein-coupled receptor S1P1/EDG1 and have a powerful and long-lasting immunomodulating effect which is achieved by reducing the number of circulating and infiltrating T- and B-lymphocytes, without affecting their maturation, memory, or expansion. The reduction of circulating T-/B-lymphocytes as a result of S1P1/EDG1 agonism, possibly in combination with the observed improvement of endothelial cell layer function associated with S1P1/EDG1 activation, makes such compounds useful to treat uncontrolled inflammatory disease and to improve vascular functionality.

The compounds of the present invention can be utilized alone or in combination with standard drugs inhibiting T-cell activation, to provide a new immunomodulating therapy with a reduced propensity for infections when compared to standard immunosuppressive therapy. Furthermore, the compounds of the present invention can be used in combination with reduced dosages of traditional immunosuppressant therapies, to provide on the one hand effective immunomodulating activity, while on the other hand reducing end organ damage associated with higher doses of standard immunosuppressive drugs. The observation of improved endothelial cell layer function associated with S1P1/EDG1 activation provides additional benefits of compounds to improve vascular function.

The nucleotide sequence and the amino acid sequence for the human S1P1/EDG1 receptor are known in the art and are published in e.g.: Hla, T., and Maciag, T. *J. Biol Chem.* 265 (1990), 9308-9313; WO 91/15583 published 17 Oct. 1991; WO 99/46277 published 16 Sep. 1999. The potency and efficacy of the compounds of Formula (I) are assessed using a GTPγS assay to determine $EC_{50}$ values and by measuring the circulating lymphocytes in the rat after oral administration, respectively (see in Examples).

The general terms used hereinbefore and hereinafter preferably have, within this disclosure, the following meanings, unless otherwise indicated:

Where the plural form is used for compounds, salts, pharmaceutical compositions, diseases and the like, this is intended to mean also a single compound, salt, or the like.

Any reference hereinbefore or hereinafter to a compound of Formula (I) is to be understood as referring also to salts, especially pharmaceutically acceptable salts, of a compound of Formula (I), as appropriate and expedient.

The term $C_{1-5}$-alkyl, alone or in combination with other groups, means saturated, branched or preferably straight chain groups with one to five carbon atoms. Preferred examples of $C_{1-5}$-alkyl groups are methyl, ethyl, n-propyl, n-butyl, iso-butyl, and n-pentyl.

The term $C_{1-4}$-alkyl, alone or in combination with other groups, means saturated, branched or preferably straight chain groups with one to four carbon atoms, preferably one to three carbon atoms, i.e. $C_{1-3}$-alkyl. Preferred examples of $C_{1-4}$-alkyl groups are methyl, ethyl, and n-propyl.

Likewise, the term $C_{2-5}$-alkyl, alone or in combination with other groups, means saturated, branched or straight chain groups with two to five carbon atoms. Preferred examples of $C_{2-5}$-alkyl groups are ethyl, n-propyl, n-butyl, iso-butyl, n-pentyl, and iso-pentyl.

The term $C_{1-5}$-alkoxy, alone or in combination with other groups, means an R—O group, wherein R is a $C_{1-5}$-alkyl.

The term $C_{1-4}$-alkoxy, alone or in combination with other groups, means an R—O group, wherein R is a $C_{1-4}$-alkyl. Preferred examples of $C_{1-4}$-alkoxy groups are methoxy, ethoxy, propoxy, iso-propoxy, and iso-butoxy.

The term $C_{2-5}$-alkoxy, alone or in combination with other groups, means an R—O group, wherein R is a $C_{2-5}$-alkyl.

The term halogen means fluoro, chloro, bromo or iodo, preferably fluoro or chloro.

Salts are preferably the pharmaceutically acceptable salts of the compounds of Formula (I).

The term "pharmaceutically acceptable salts" refers to non-toxic, inorganic or organic acid and/or base addition salts, Lit.: e.g. "Salt selection for basic drugs", *Int. J. Pharm.* (1986), 33, 201-217.

The compounds of Formula (I) may contain one or more stereogenic or asymmetric centers, such as one or more asymmetric carbon atoms. Substituents at a double bond or a ring may be present in cis- (═Z—) or trans (═E—) form unless indicated otherwise. The compounds of Formula (I) may thus be present as mixtures of stereoisomers or preferably as pure stereoisomers. Mixtures of stereoisomers may be separated in a manner known to a person skilled in the art.

i) The invention relates to novel thiophene compounds of the Formula (I),

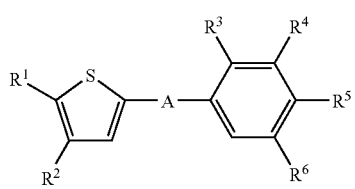

Formula (I)

wherein

A represents *—CO—CH$_2$CH$_2$—, *—CO—CH═CH—,

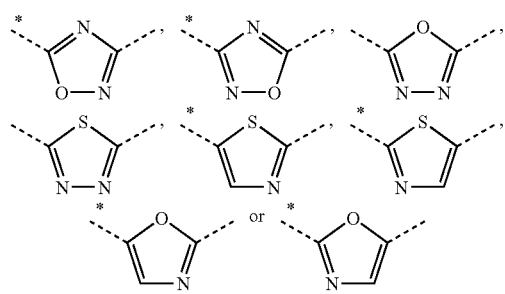

wherein the asterisks indicate the bond that is linked to the thiophene group of Formula (I);

$R^1$ represents $C_{2-5}$-alkyl;

$R^2$ represents hydrogen, methyl or ethyl;

$R^3$ represents hydrogen, $C_{1-4}$-alkyl, $C_{1-4}$-alkoxy, or halogen;

$R^4$ represents hydrogen, $C_{1-4}$-alkyl, $C_{1-4}$-alkoxy, halogen, trifluoromethyl or trifluoromethoxy;

$R^5$ represents hydrogen, hydroxy-$C_{1-5}$-alkyl, 2,3-dihydroxypropyl, di-(hydroxy-$C_{1-4}$-alkyl)-$C_{1-4}$-alkyl, —CH$_2$—(CH$_2$)$_n$—NHSO$_2$R$^{51}$, —(CH$_2$)$_n$CH(OH)—CH$_2$—NHSO$_2$R$^{51}$, —CH$_2$—(CH$_2$)$_n$—NHCOR$^{52}$, —(CH$_2$)$_n$CH(OH)—CH$_2$—NHCOR$^{52}$, —CH$_2$—(CH$_2$)$_n$—CONR$^{53}$R$^{54}$, —CO—NHR$^{53}$, 1-(3-carboxy-azetidinyl)-2-acetyl, 1-(2-carboxy-pyrrolidinyl)-2-acetyl, 1-(3-carboxy-pyrrolidinyl)-2-acetyl, 1-(3-carboxy-azetidinyl)-3-propionyl, 1-(2-carboxy-pyrrolidinyl)-3-propionyl, 1-(3-carboxy-pyrrolidinyl)-3-propionyl, hydroxy, $C_{1-5}$-alkoxy, hydroxy-$C_{2-5}$-alkoxy, di-(hydroxy-$C_{1-4}$-alkyl)-$C_{1-4}$-alkoxy, 2,3-dihydroxypropoxy, 2-hydroxy-3-methoxy-propoxy, —OCH$_2$—(CH$_2$)$_m$—NHSO$_2$R$^{51}$, —OCH$_2$—CH(OH)—CH$_2$—NHSO$_2$R$^{51}$, —OCH$_2$—(CH$_2$)$_m$—NHCOR$^{52}$, or —OCH$_2$—CH(OH)—CH$_2$—NHCOR$^{52}$;

$R^{51}$ represents $C_{1-3}$-alkyl, methylamino, ethylamino, or dimethylamino;

$R^{52}$ represents hydroxymethyl, 2-hydroxyethyl, 2-hydroxy-1-hydroxymethyl-ethyl, or 2,3-dihydroxypropyl;

$R^{53}$ represents hydrogen, $C_{1-3}$-alkyl, 2-hydroxyethyl, 2-hydroxy-1-hydroxymethyl-ethyl, 2,3-dihydroxypropyl, carboxymethyl, 1-($C_{1-5}$-alkylcarboxy)methyl, 2-carboxyethyl, or 2-($C_{1-5}$-alkylcarboxy)ethyl;

$R^{54}$ represents hydrogen, or methyl;

m represents the integer 1 or 2;

n represents 0, 1, or 2; and $R^6$ represents hydrogen, $C_{1-4}$-alkyl or halogen;

and salts thereof.

ii) A particular embodiment of the invention relates to thiophene derivatives according to embodiment i), wherein A represents

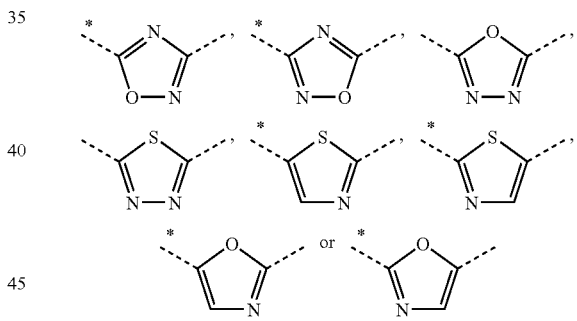

wherein the asterisks indicate the bond that is linked to the thiophene group of Formula (I), and salts thereof.

iii) Another particular embodiment of the invention relates to thiophene derivatives according to embodiment i), wherein A represents

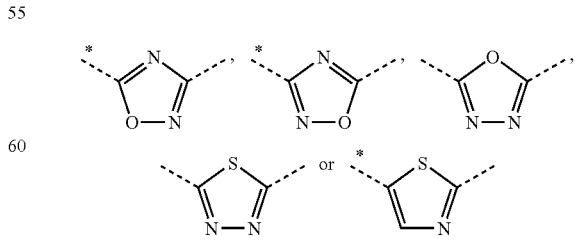

wherein the asterisks indicate the bond that is linked to the thiophene group of Formula (I), and salts thereof.

iv) Another particular embodiment of the invention relates to thiophene derivatives according to embodiment i), wherein A represents

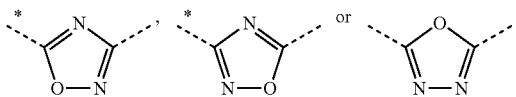

wherein the asterisks indicate the bond that is linked to the thiophene group of Formula (I), and salts thereof.

v) Another particular embodiment of the invention relates to thiophene derivatives according to embodiment i), wherein A represents

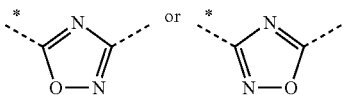

wherein the asterisks indicate the bond that is linked to the thiophene group of Formula (I), and salts thereof.

vi) Another particular embodiment of the invention relates to thiophene derivatives according to embodiment i), wherein A represents

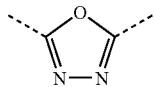

and salts thereof.

vii) Another particular embodiment of the invention relates to thiophene derivatives according to any one of the embodiments i) to vi), wherein $R^1$ represents n-propyl or isobutyl, and salts thereof.

viii) Another particular embodiment of the invention relates to thiophene derivatives according to any one of the embodiments i) to vii), wherein $R^2$ represents hydrogen or methyl, and salts thereof.

ix) A preferred embodiment of the invention relates to thiophene derivatives according to any one of the embodiments i) to vii), wherein $R^2$ represents hydrogen, and salts thereof.

x) Another preferred embodiment of the invention relates to thiophene derivatives according to any one of the embodiments i) to ix), wherein $R^3$ represents methoxy, and $R^4$ and $R^6$ represent hydrogen, and salts thereof.

xi) Another preferred embodiment of the invention relates to thiophene derivatives according to any one of the embodiments i) to ix), wherein $R^3$ represents hydrogen, $R^4$ represents methyl, ethyl, or methoxy, and $R^6$ represents methyl, ethyl or halogen, and salts thereof.

xii) Another preferred embodiment of the invention relates to thiophene derivatives according to any one of the embodiments i) to ix), wherein $R^3$ represents hydrogen, and $R^4$ and $R^6$ represent a methyl group, and salts thereof.

xiii) A particularly preferred embodiment of the invention relates to thiophene derivatives according to any one of the embodiments i) to ix), wherein $R^3$ represents hydrogen, $R^4$ represents a methyl group, and $R^6$ represents an ethyl group, and salts thereof.

xiv) Another preferred embodiment of the invention relates to thiophene derivatives according to any one of the embodiments i) to ix), wherein $R^3$ represents hydrogen, $R^4$ represents a methoxy group, and $R^6$ represents a chlorine atom, and salts thereof.

xv) Another preferred embodiment of the invention relates to thiophene derivatives according to any one of the embodiments i) to ix), wherein $R^3$ represents hydrogen, $R^4$ represents a methyl group, and $R^6$ represents a chlorine atom, and salts thereof.

xvi) Another preferred embodiment of the invention relates to thiophene derivatives according to any one of the embodiments i) to xv), wherein $R^5$ represents 2,3-dihydroxypropyl, —$CH_2$—$(CH_2)_n$—$NHCOR^{52}$, —$(CH_2)_n CH(OH)$—$CH_2$—$NHCOR^{52}$, hydroxy, hydroxy-$C_{2-5}$-alkoxy, di-(hydroxy-$C_{1-4}$-alkyl)-$C_{1-4}$-alkoxy, 2,3-dihydroxypropoxy, 2-hydroxy-3-methoxy-propoxy, —$OCH_2$—$(CH_2)_m$—$NHCOR^{52}$, or —$OCH_2$—$CH(OH)$—$CH_2$—$NHCOR^{52}$, and salts thereof.

xvii) Another preferred embodiment of the invention relates to thiophene derivatives according to any one of the embodiments i) to xv), wherein $R^5$ represents hydroxy, hydroxy-$C_{2-5}$-alkoxy, di-(hydroxy-$C_{1-4}$-alkyl)-$C_{1-4}$-alkoxy, 2,3-dihydroxypropoxy, 2-hydroxy-3-methoxy-propoxy, —$OCH_2$—$(CH_2)_m$—$NHCOR^{52}$, or —$OCH_2$—$CH(OH)$—$CH_2$—$NHCOR^{52}$, and salts thereof.

xviii) Another preferred embodiment of the invention relates to thiophene derivatives according to any one of the embodiments i) to xv), wherein $R^5$ represents 3-hydroxy-2-hydroxymethyl-propoxy, 2,3-dihydroxypropoxy, or —$OCH_2$—$CH(OH)$—$CH_2$—$NHCOR^{52}$, and salts thereof.

xix) Another preferred embodiment of the invention relates to thiophene derivatives according to any one of the embodiments i) to xv), wherein $R^5$ represents 2,3-dihydroxypropoxy, or —$OCH_2$—$CH(OH)$—$CH_2$—$NHCOR^{52}$, wherein $R^{52}$ represents hydroxymethyl, and salts thereof.

xx) An especially preferred embodiment of the invention relates to thiophene derivatives according to embodiment i), wherein A represents

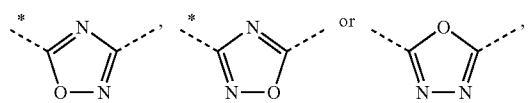

wherein the asterisks indicate the bond that is linked to the thiophene group of Formula (I); $R^1$ represents n-propyl or isobutyl; $R^2$ represents hydrogen; $R^3$ represents hydrogen or methoxy; $R^4$ represents hydrogen, methyl, ethyl or methoxy; $R^5$ represents 3-hydroxy-2-hydroxymethyl-propoxy, 2,3-dihydroxypropoxy, or —$OCH_2$—$CH(OH)$—$CH_2$—$NHCOR^{52}$; and $R^6$ represents hydrogen, methyl, ethyl or chlorine; and salts thereof.

xxi) Another especially preferred embodiment of the invention relates to thiophene derivatives according to embodiment i), wherein A represents *—CO—$CH_2CH_2$—, *—CO—CH=CH—,

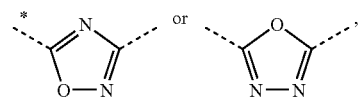

wherein the asterisks indicate the bond that is linked to the thiophene group of Formula (I);
$R^1$ represents $C_{2-5}$-alkyl;
$R^2$ and $R^3$ both represent hydrogen;
$R^4$ represents $C_{1-4}$-alkyl;

R⁵ represents hydroxy, 2,3-dihydroxypropoxy, or —OCH$_2$—CH(OH)—CH$_2$—NHCOR$^{52}$;
R$^{52}$ represents hydroxymethyl; and
R represents C$_{1-4}$-alkyl;
and salts thereof.

xxii) Especially preferred thiophene compounds according to Formula (I) are:
(2R)—N-(3-{4-[5-(5-ethyl-thiophen-2-yl)-[1,2,4]oxadiazol-3-yl]-2,6-dimethyl-phenoxy}-2-hydroxy-propyl)-2-hydroxy-acetamide,
(2S)—N-(3-{4-[5-(5-ethyl-thiophen-2-yl)-[1,2,4]oxadiazol-3-yl]-2,6-dimethyl-phenoxy}-2-hydroxy-propyl)-2-hydroxy-acetamide,
(2R)—N-(3-{2,6-dimethyl-4-[5-(5-butyl-thiophen-2-yl)-[1,2,4]oxadiazol-3-yl]-phenoxy}-2-hydroxy-propyl)-2-hydroxy-acetamide,
(2S)—N-(3-{2,6-dimethyl-4-[5-(5-butyl-thiophen-2-yl)-[1,2,4]oxadiazol-3-yl]-phenoxy}-2-hydroxy-propyl)-2-hydroxy-acetamide,
(2R)—N-(3-{2,6-dimethyl-4-[5-(5-isobutyl-thiophen-2-yl)-[1,2,4]oxadiazol-3-yl]-phenoxy}-2-hydroxy-propyl)-2-hydroxy-acetamide,
(2S)—N-(3-{2,6-dimethyl-4-[5-(5-isobutyl-thiophen-2-yl)-[1,2,4]oxadiazol-3-yl]-phenoxy}-2-hydroxy-propyl)-2-hydroxy-acetamide,
(2R)—N-(3-{2-ethyl-6-methyl-4-[5-(5-isobutyl-thiophen-2-yl)-[1,2,4]oxadiazol-3-yl]-phenoxy}-2-hydroxy-propyl)-2-hydroxy-acetamide,
(2S)—N-(3-{2-ethyl-6-methyl-4-[5-(5-isobutyl-thiophen-2-yl)-[1,2,4]oxadiazol-3-yl]-phenoxy}-2-hydroxy-propyl)-2-hydroxy-acetamide,
(2R)—N-(3-{2,6-dimethyl-4-[5-(5-propyl-thiophen-2-yl)-[1,2,4]oxadiazol-3-yl]-phenoxy}-2-hydroxy-propyl)-2-hydroxy-acetamide,
(2S)—N-(3-{2,6-dimethyl-4-[5-(5-propyl-thiophen-2-yl)-[1,2,4]oxadiazol-3-yl]-phenoxy}-2-hydroxy-propyl)-2-hydroxy-acetamide,
(2R)—N-(3-{2-ethyl-6-methyl-4-[5-(5-propyl-thiophen-2-yl)-[1,2,4]oxadiazol-3-yl]-phenoxy}-2-hydroxy-propyl)-2-hydroxy-acetamide,
(2S)—N-(3-{2-ethyl-6-methyl-4-[5-(5-propyl-thiophen-2-yl)-[1,2,4]oxadiazol-3-yl]-phenoxy}-2-hydroxy-propyl)-2-hydroxy-acetamide,
(2R)—N-(3-{2-ethyl-4-[5-(5-isobutyl-thiophen-2-yl)-[1,2,4]oxadiazol-3-yl]-6-methyl-phenoxy}-2-hydroxy-propyl)-2-hydroxy-acetamide,
(2S)—N-(3-{2-ethyl-4-[5-(5-isobutyl-thiophen-2-yl)-[1,2,4]oxadiazol-3-yl]-6-methyl-phenoxy}-2-hydroxy-propyl)-2-hydroxy-acetamide,
(2R)-3-{4-[5-(5-isobutyl-thiophen-2-yl)-[1,3,4]oxadiazol-2-yl]-2,6-dimethyl-phenoxy}-propane-1,2-diol,
(2S)-3-{4-[5-(5-isobutyl-thiophen-2-yl)-[1,3,4]oxadiazol-2-yl]-2,6-dimethyl-phenoxy}-propane-1,2-diol,
(2R)-2-hydroxy-N-(2-hydroxy-3-{4-[5-(5-isobutyl-thiophen-2-yl)-[1,3,4]oxadiazol-2-yl]-2,6-dimethyl-phenoxy}-propyl)-acetamide,
(2S)-2-hydroxy-N-(2-hydroxy-3-{4-[5-(5-isobutyl-thiophen-2-yl)-[1,3,4]oxadiazol-2-yl]-2,6-dimethyl-phenoxy}-propyl)-acetamide,
(2R)-2-hydroxy-N-(2-hydroxy-3-{4-[5-(5-isobutyl-thiophen-2-yl)-[1,3,4]oxadiazol-2-yl]-2-ethyl-6-methyl-phenoxy}-propyl)-acetamide, and
(2S)-2-hydroxy-N-(2-hydroxy-3-{4-[5-(5-isobutyl-thiophen-2-yl)-[1,3,4]oxadiazol-2-yl]-2-ethyl-6-methyl-phenoxy}-propyl)-acetamide,
and salts of these compounds.

xxiii) Further especially preferred thiophene compounds according to Formula (I) are:
2-hydroxy-N-((2S)-2-hydroxy-3-{4-[5-(5-isobutyl-thiophen-2-yl)-[1,3,4]oxadiazol-2-yl]-2,6-dimethyl-phenoxy}-propyl)-acetamide,
N-((2S)-3-{2-ethyl-6-methyl-4-[5-(5-propyl-thiophen-2-yl)-[1,3,4]oxadiazol-2-yl]-phenoxy}-2-hydroxy-propyl)-2-hydroxy-acetamide,
(2R)-3-{2-ethyl-4-[5-(5-isobutyl-4-methyl-thiophen-2-yl)-[1,3,4]oxadiazol-2-yl]-6-methyl-phenoxy}-propane-1,2-diol,
(2S)-3-{2-ethyl-4-[5-(5-isobutyl-4-methyl-thiophen-2-yl)-[1,3,4]oxadiazol-2-yl]-6-methyl-phenoxy}-propane-1,2-diol,
N-((2R)-3-{2-ethyl-4-[5-(5-isobutyl-4-methyl-thiophen-2-yl)-[1,3,4]oxadiazol-2-yl]-6-methyl-phenoxy}-2-hydroxy-propyl)-2-hydroxy-acetamide, and
N-((2S)-3-{2-ethyl-4-[5-(5-isobutyl-4-methyl-thiophen-2-yl)-[1,3,4]oxadiazol-2-yl]-6-methyl-phenoxy}-2-hydroxy-propyl)-2-hydroxy-acetamide,
and salts of these compounds.

The compounds of Formula (I) and their pharmaceutically acceptable salts can be used as medicaments, e.g. in the form of pharmaceutical compositions for enteral or parental administration.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, *The Science and Practice of Pharmacy,* 20th Edition, Philadelphia College of Pharmacy and Science) by bringing the described compounds of Formula (I) or their pharmaceutically acceptable salts, optionally in combination with other therapeutically valuable substances, into a galenical administration form together with suitable, non-toxic, inert, pharmaceutically acceptable solid or liquid carrier materials and, if desired, usual pharmaceutical adjuvants.

The pharmaceutical compositions comprising a compound of Formula (I) are useful for the prevention and/or treatment of diseases or disorders associated with an activated immune system.

Such diseases or disorders are selected from the group consisting of rejection of transplanted organs, tissue or cells; graft-versus-host diseases brought about by transplantation; autoimmune syndromes including rheumatoid arthritis; systemic lupus erythematosus; antiphospholipid syndrome; Hashimoto's thyroiditis; lymphocytic thyroiditis; multiple sclerosis; myasthenia gravis; type I diabetes; uveitis; episcleritis; scleritis; Kawasaki's disease, uveo-retinitis; posterior uveitis; uveitis associated with Behcet's disease; uveo-meningitis syndrome; allergic encephalomyelitis; chronic allograft vasculopathy; post-infectious autoimmune diseases including rheumatic fever and post-infectious glomerulonephritis; inflammatory and hyperproliferative skin diseases; psoriasis; psoriatic arthritis; atopic dermatitis; myopathy; myositis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; scleroderma; alopecia areata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' ophthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchiolitis; bronchitis; endometriosis; orchitis; gastric ulcers; ischemic bowel diseases; inflammatory bowel diseases; necrotizing enterocolitis; intestinal lesions associated with thermal burns; coeliac disease; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; tubulointerstitial nephritis; interstitial cystitis; multiple myositis; Guillain-Barré syndrome; Meniere's disease; polyneuritis; multiple neuritis; myelitis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; autoimmune thrombocytopenia; agranulocytosis; pernicious anemia; megaloblastic anemia; anerythroplasia; osteoporosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; myocarditis; scleroderma; Wegener's granuloma; Sjogren's syndrome; adiposis; eosinophilic fascitis; lesions of gingiva, periodontium, alveolar bone, substantia ossea dentis; male pattern alopecia or alopecia senilis; muscular dystrophy; pyoderma; Sezary's syndrome; hypophysitis; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic leukemias; lymphoma; pulmonary emphysema; cataracta; siderosis; retinitis pigmentosa; senile macular degeneration; vitreal scarring; corneal alkali burn; dermatitis erythema; ballous dermatitis; cement dermatitis; gingivitis; periodontitis; sepsis; pancreatitis; peripheral artery disease; carcinogenesis; solid cancer tumors; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; and "acute-on-chronic" liver failure.

Preferred diseases or disorders to be treated and/or prevented with the compounds of Formula (I) are selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, uveoretinitis; atopic diseases such as rhinitis, conjunctivitis, dermatitis; asthma; type I diabetes; post-infectious autoimmune diseases including rheumatic fever and post-infectious glomerulonephritis; solid cancers and tumor metastasis.

Particularly preferred diseases or disorders to be treated and/or prevented with the compounds of Formula (I) are selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis.

The present invention also relates to a method for the prevention or treatment of a disease or disorder mentioned herein comprising administering to a subject a pharmaceutically active amount of a compound of Formula (I).

Furthermore, compounds of the Formula (I) are also useful, in combination with one or several immunomodulating agents, for the prevention and/or treatment of the diseases and disorders mentioned herein. According to a preferred embodiment of the invention, said agents are selected from the group consisting of immunosuppressants, corticosteroids, NSAID's, cytotoxic drugs, adhesion molecule inhibitors, cytokines, cytokine inhibitors, cytokine receptor antagonists and recombinant cytokine receptors.

The present invention also relates to the use of a compound of Formula (I) for the preparation of a pharmaceutical composition, optionally for use in combination with one or several immunomodulating agents, for the prevention or treatment of the diseases and disorders mentioned herein.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

Compounds of the Formula (I) of the present invention can be prepared according to the general sequence of reactions outlined below. Only a few of the synthetic possibilities leading to compounds of Formula (I) are described.

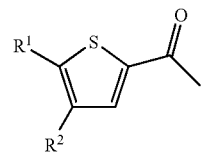

Structure 1

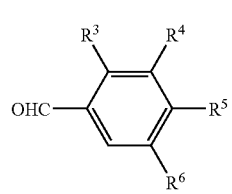

Structure 2

In case A represents —CO—CH=CH—, the compounds of Formula (I) may be prepared by reacting a compound of Structure 1 with a compound of Structure 2 in the presence of a base or an acid. The functional groups present in the residues $R^3$ to $R^6$ may require temporary protection or may even be introduced in additional steps that follow the condensation reaction. Compounds of Formula (I) wherein A represents —CO—CH$_2$—CH$_2$— may be prepared by reacting a compound of Formula (I) wherein A represents —CO—CH=CH— with hydrogen in the presence of a catalyst such as Pd/C, Pt/C, PtO$_2$, etc. in a solvent such as ethanol, methanol, THF, etc. or mixtures thereof.

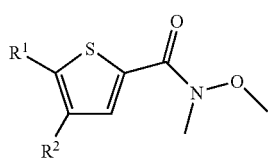

Structure 3

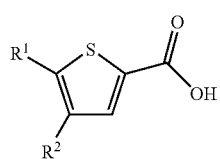

Structure 4

A compound of Structure 1 may be prepared by reacting a compound of Structure 3 with a methyl Grignard reagent or by treating a compound of Structure 4 with 2 equivalents of methyllithium in a solvent such as diethyl ether, THF, etc. at temperatures between −20 and 50° C. The Weinreb amide compound of Structure 3 is prepared by treating a compound of Structure 4 with N,O-dimethylhydroxylamine hydrochloride in the presence of coupling reagent such as EDC, DCC, etc. (M. Mentzel, H. M. R. Hoffmann, N-Methoxy N-methyl amides (Weinreb amides) in modern organic synthesis, *Journal fuer Praktische Chemie/Chemiker-Zeitung* 339 (1997), 517-524; J. Singh, N. Satyamurthi, I. S. Aidhen, The growing synthetic utility of Weinreb's amide, *Journal fuer Praktische Chemie* (Weinheim, Germany) 342 (2000) 340-347; V. K. Khlestkin, D. G. Mazhukin, Recent advances in the application of N,O-dialkylhydroxylamines in organic chemistry, *Current Organic Chemistry* 7 (2003), 967-993).

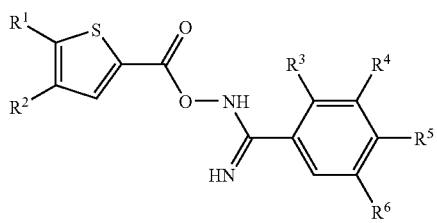

Structure 5

Compounds of Formula (I) which represent a 5-thienyl-[1,2,4]oxadiazole derivative, are prepared by reacting a compound of Structure 5 in a solvent such as xylene, toluene, benzene, pyridine, DMF, dichloromethane, acetic acid, trifluoroacetic acid, etc. at rt or elevated temperatures in the presence or absence of auxiliaries such as acids (e.g. TFA, acetic acid, HCl, etc.), bases (e.g. NaH, NaOAc, $Na_2CO_3$, $K_2CO_3$, triethylamine, etc.), tetraalkylammonium salts, or water removing agents (e.g. oxalyl chloride, a carboxylic acid anhydride, $POCl_3$, $PCl_5$, $P_4O_{10}$, molecular sieves, methoxycarbonylsulfamoyl triethylammonium hydroxide (Burgess reagent), etc.) (Lit.: e.g. A. R. Gangloff, J. Litvak, E. J. Shelton, D. Sperandio, V. R. Wang, K. D. Rice, *Tetrahedron Lett.* 42 (2001), 1441-1443; T. Suzuki, K. Iwaoka, N. Imanishi, Y. Nagakura, K. Miyta, H. Nakahara, M. Ohta, T. Mase, *Chem. Pharm. Bull.* 47 (1999), 120-122; R. F. Poulain, A. L. Tartar, B. P. Déprez, *Tetrahedron Lett.* 42 (2001), 1495-1498; R. M. Srivastava, F. J. S. Oliveira, D. S. Machado, R. M. Souto-Maior, *Synthetic Commun.* 29 (1999), 1437-1450; E. O. John, J. M. Shreeve, *Inorganic Chemistry* 27 (1988), 3100-3104; B. Kaboudin, K. Navaee, *Heterocycles* 60 (2003), 2287-2292).

Compounds of Structure 5 may be prepared by reacting a compound of Structure 4 with a compound of Structure 6 in a solvent such as DMF, THF, DCM, etc. in the presence or absence of one ore more coupling agents such as TBTU, DCC, EDC, HBTU, HOBt, CDI, etc. and in the presence or absence of a base such as triethylamine, Hünig's base, NaH, $K_2CO_3$, etc. (Lit.: e.g. A. Hamze, J.-F. Hernandez, P. Fulcrand, J. Martinez, *J. Org. Chem.* 68 (2003) 7316-7321; and the literature cited above).

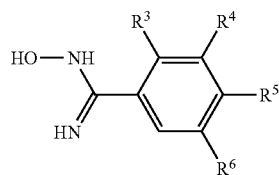

Structure 6

Compounds of Formula (I) which represent a 3-thienyl-[1,2,4]oxadiazole derivative are prepared in an analogous fashion (Lit.: e.g. C. T. Brain, J. M. Paul, Y. Loong, P. J. Oakley, *Tetrahedron Lett.* 40 (1999) 3275-3278) by reacting a compound of Structure 7 with a compound of Structure 8 and subsequent cyclisation of the corresponding hydroxyamidine ester intermediate.

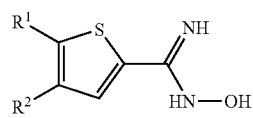

Structure 7

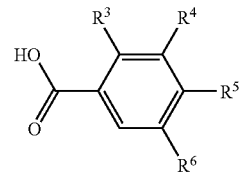

Structure 8

Compounds of Structure 6 and 7 may be prepared by reacting a compound of Structure 9 and 10, respectively, with hydroxylamine or one of its salts in a solvent such as methanol, ethanol, pyridine, etc. in the presence or absence of a base such as $Na_2CO_3$, $K_2CO_3$, potassium tert.-butylate, triethylamine, etc. (Lit.: e.g. T. Suzuki, K. Iwaoka, N. Imanishi, Y. Nagakura, K. Miyta, H. Nakahara, M. Ohta, T. Mase, *Chem. Pharm. Bull.* 47 (1999), 120-122; J. Cui, D. Crich, D. Wink, M. Lam, A. L. Rheingold, D. A. Case, W. T. Fu, Y. Zhou, M. Rao, A. J. Olson, M. E. Johnson, *Bioorg. Med. Chem.* 11 (2003), 3379-3392; R. Miller, F. Lang, Z. J. Song, D. Zewge, WO 2004/035538 (Merck & Co., Inc., USA); B. Kaboudin, K. Navaee, *Heterocycles* 60 (2003), 2287-2292).

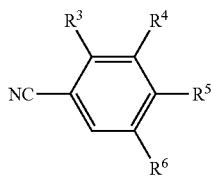

Structure 9

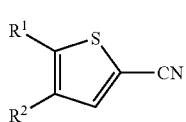

Structure 10

Depending on the nature of the functionalities present in the residues $R^3$ to $R^6$ in Structures 2, 5, 6, 8, and 9, these functionalities may require temporary protection. Appropriate protecting groups are known to a person skilled in the art and include e.g. a benzyl or a trialkylsilyl group to protect an alcohol, a ketal to protect a diol, etc. These protecting groups may be employed according to standard methodology (e.g. T. W. Greene, P. G. M. Wuts, Protective Groups in Organic Synthesis, $3^{rd}$ Edition, Wiley New York, 1991; P. J. Kocienski, Protecting Groups, Thieme Stuttgart, 1994). Alternatively, the desired residues $R^3$ to $R^6$, in particular $R^5$, may also be introduced in later steps that follow the coupling of the thiophene compounds of Structure 1, 4, and 7 with the phenyl derivatives of Structure 2, 6, and 8, respectively, by using a suitable precursor of a compound of Structure 2, 6, and 8. The phenyl compounds of Structure 2, 6, 8 and 9 or their precursors are either commercially available or are prepared according to procedures known to a person skilled in the art.

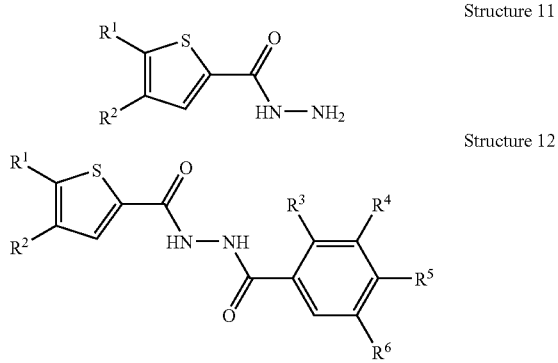

Structure 11

Structure 12

Compounds of Formula (I) which represent a 2-thienyl-[1,3,4]oxadiazole or a 2-thienyl-[1,3,4]thiadiazole derivative are prepared similarly by reacting a compound of Structure 4 with hydrazine (by using a coupling reagent such as TBTU, DCC, EDC, HBTU, PyBOP, HOBt, CDI, etc.) to form a compound of Structure 11 which is then coupled with a compound of Structure 8 to give a compound of Structure 12. A compound of Structure 12 can also be prepared by following the reverse reaction order i.e. by first coupling a compound of Structure 8 with hydrazine followed by reacting the corresponding hydrazide intermediate with a compound of Structure 4. Dehydration of a compound of Structure 12 to form the desired 2-thienyl-[1,3,4]oxadiazole derivative is affected by treating a compound of Structure 12 with a reagent such as $POCl_3$, $CCl_4$ or $CBr_4$ in combination with triphenylphosphine, $P_2O_5$, Burgess reagent, etc. in a solvent such as toluene, acetonitrile, dioxane, THF, or $CHCl_3$ at temperatures between 20 and 120° C. in the presence or absence of microwave irradiation. (Lit.: e.g. M. A. Garcia, S. Martin-Santamaria, M. Cacho, F. Moreno de la Llave, M. Julian, A. Martinez, B. De Pascual-Teresa, A. Ramos, *J. Med. Chem.* 48 (2005) 4068-4075; C. T. Brain, J. M. Paul, Y. Loong, P. J. Oakley, *Tetrahedron Lett.* 40 (1999) 3275-3278). Likewise, 2-thienyl-[1,3,4]thiadiazole derivatives are obtained by cyclising a compound of Structure 12 with Lawesson's reagent optionally in combination with $P_2S_5$ in the absence or presence of a solvent such as pyridine, toluene, THF, or acetonitrile at elevated temperatures with or without microwave irradiation (Lit.: e.g. A. A. Kiryanov, P. Sampson, A. J. Seed, *J. Org. Chem.* 66 (2001) 7925-7929).

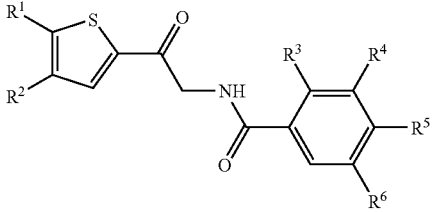

Structure 13

Compounds of Formula (I) which represent a 5-thienyl-oxazole or a 5-thienyl-thiazole derivative are prepared by treating a compound of Structure 13 either with $POCl_3$, $PCl_5$, $I_2$ in combination with triphenylphosphine and triethylamine, Burgess reagent, trifluoracetic anhydride, etc. in a solvent such as toluene, benzene, dioxane, or THF at temperatures between 20 and 120° C., or with Lawesson's reagent, optionally in combination with $P_2S_5$, in the presence or absence of a solvent such as pyridine, toluene, THF, or acetonitrile at elevated temperatures with or without microwave irradiation as mentioned above (Lit.: e.g. N. Sato, T. Shibata, M. Jitsuoka, T. Ohno, T. Takahashi, T. Hirohashi, T. Kanno, H. Iwaasa, A. Kanatani, T. Fukami, Takehiro, *Bioorg. & Med. Chem. Lett.* 14 (2004) 1761-1764). The compounds of Structure 13 are prepared by reacting a compound of Structure 14 with a compound of Structure 9. The aminoketon of Structure 14 can be prepared from a compound of Structure 1 by procedures given in the literature (e.g. J. L. LaMattina, *J. Heterocyclic Chem.* 20 (1983) 533-538; M. Pesson, M. Antoine, P. Girard, J. L. Benichon, S. Chabassier, P. De Lajudie, S. Patte, F. Roquet, G. Montay, *Eur. J. Med. Chem.* 15 (1980) 263-268). Compounds of Formula (I) which represent a 2-thienyl-oxazole or a 2-thienyl-thiazole derivative are prepared in an analogous fashion from a compound of Structure 15 and a compound of Structure 4.

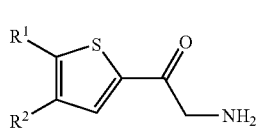

Structure 14

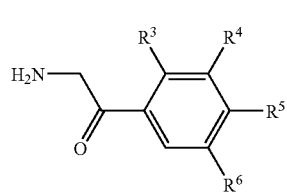

Structure 15

Alternatively, the bonds between the thiophene or the phenyl ring and the central 5-membered heteroaromatic ring can also be formed by applying palladium catalysed cross coupling reactions.

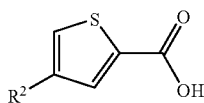

Structure 16

The compounds of Structure 4 can be prepared by alkylating a thiophene-2-carboxylic acid of Structure 16 according to literature procedures (e.g. D. W. Knight, A. P. Nott, *J. Chem. Soc. Perkin Trans.* 1 1983 791-794). The thiophene-2-carboxylic acids of Structure 16 or their methyl or ethyl esters are either commercially available or can be prepared following literature procedures (e.g. S. Gronowitz, T. Klingstedt, L. Svensson, U. Hansson, *Lipids* 28 (1993) 889-897).

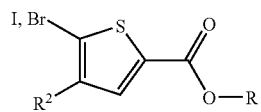

Structure 17

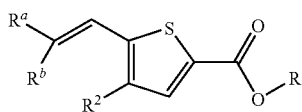

Structure 18

The compounds of Structure 4 may also be prepared by reacting a compound of Structure 17, wherein R represents methyl, ethyl, tert. butyl, etc. with a 2,4,6-trialkenylcyclotriboroxane under Suzuki conditions (Lit.: e.g. F. Kerins, D. F. O'Shea, *J. Org. Chem.* 67 (2002) 4968-4971) to give a compound of Structure 18, wherein R represents methyl, ethyl, tert.-butyl, etc. and $R^a$ and $R^b$ both independently represent hydrogen, methyl, ethyl, etc., which upon hydrogenation and subsequent ester cleavage furnishes the desired compound of Structure 4. Compounds of Structure 17 are either commercially available or are prepared according to literature procedures.

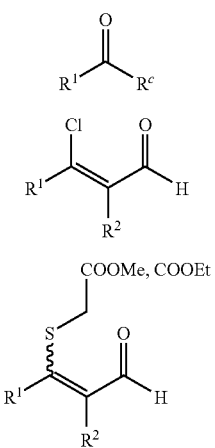

Structure 19

Structure 20

Structure 21

Compounds of Structure 4, wherein $R^2$ represents methyl or ethyl, may also be prepared by reacting a compound of Structure 19, wherein $R^c$ represents ethyl or n-propyl, with $POCl_3$ in DMF under Vilsmeyer conditions to give a compound of Structure 20 (Lit.: e.g. G. Alvernhe, D. Greif, B. Langlois, A. Laurent, I. Le Dréan, M. Pulst, A. Selmi, M. Weissenfels, *Bull. Soc. Chim. Fr.* 131 (1994) 167-172). The compound of Structure 20 is treated with a mercaptoacetic acid ester in the presence of a base such a NaH, NaOEt, NaOMe, K tert.-butoxide, etc., in THF, dioxane, DMF, ethanol, methanol, etc., or mixtures thereof, to form an intermediate of Structure 21. Cyclisation under basic conditions using a non aqueous base such as NaOMe, NaOEt, KOtBu, DBU, etc., in a solvent such as methanol, ethanol, THF, DMF, etc., or mixtures thereof, preferably at elevated temperatures, followed by saponification with an aqueous base such as aq. NaOH, aq. LiOH, aq. KOH, etc., or an acid such as aq. HCl, TFA, etc., in a solvent such as water, ethanol, methanol, THF, etc., or mixtures thereof, furnishes the compounds of Structure 4. Treating a compound of Structure 20 with mercaptoacetonitrile, which can be generated in situ from thioacetic acid S-cyanomethyl ester, may furnish a compound of Structure 10.

Methods that effect the transformation of a compound of Structure 4 into a compound of Structure 10, or the opposite, are known to a person skilled in the art.

EXAMPLES

The following examples illustrate the invention but do not at all limit the scope thereof.

All temperatures are stated in ° C. Compounds are characterized by $^1$H-NMR (300 MHz) or $^{13}$C-NMR (75 MHz) (Varian Oxford; chemical shifts are given in ppm relative to the solvent used; multiplicities: s=singlet, d=doublet, t=triplet, p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 μm, 120 Å, gradient: 5-95% acetonitrile in water, 1 min, with 0.04% trifluoroacetic acid, flow: 4.5 mL/min), $t_R$ is given in min; by TLC (TLC-plates from Merck, Silica gel 60 $F_{254}$); or by melting point. Compounds are purified by preparative HPLC (column: X-terra RP18, 50×19 mm, 5 μm, gradient: 10-95% acetonitrile in water containing 0.5% of formic acid) or by MPLC (Labomatic MD-80-100 pump, Linear UVIS-201 detector, column: 350×18 mm, Labogel-RP-18-5s-100, gradient: 10% methanol in water to 100% methanol).

ABBREVIATIONS

As Used Herein

| | |
|---|---|
| aq. | aqueous |
| BSA | bovine serum albumin |
| Bu | butyl |
| CC | column chromatography |
| CDI | carbonyl diimidazole |
| DBU | 1,8-diazabicylo[5.4.0]undec-7-en |
| DCC | dicyclohexyl carbodiimide |
| DCM | dichloromethane |
| DIPEA | diisopropyl-ethylamine, Hünig's base, ethyl-diisopropylamine |
| DME | 1,2-dimethoxyethane |
| DMF | dimethylformamide |
| DMSO | dimethylsulfoxide |
| EA | ethyl acetate |
| EDC | N-(3-dimethylaminopropyl)-N'-ethyl-carbodiimide |
| Et | ethyl |
| EtOH | ethanol |
| h | hour(s) |
| HBTU | O-(benzotriazol-1-yl)-N,N,N',N'-tetramethyluronium hexafluorophosphate |
| HOBt | 1-hydroxybenzotriazole |

-continued

| | |
|---|---|
| HPLC | high performance liquid chromatography |
| KOtBu | potassium tert-butoxide |
| LC-MS | liquid chromatography-mass spectrometry |
| LDA | lithium diisopropyl amide |
| Lit. | literature |
| Me | methyl |
| min | minute(s) |
| MPLC | medium pressure liquid chromatography |
| NaOAc | sodium acetate |
| NMO | N-methyl-morpholine-N-oxide |
| org. | organic |
| Ph | phenyl |
| prep. | preparative |
| PyBOP | benzotriazol-1-yl-oxy-tris-pyrrolidino-phosphonium-hexafluoro-phosphate |
| rt | room temperature |
| sat. | saturated |
| S1P | sphingosine 1-phosphate |
| TBME | tert.-butyl methyl ether |
| TBTU | 2-(1H-benzotriazole-1-yl)-1,2,3,3-tetramethyluronium tetrafluoroborate |
| TFA | trifluoroacetic acid |
| THF | tetrahydrofuran |
| TLC | thin layer chromatography |
| $t_R$ | retention time |

5-Ethyl-thiophene-2-carboxylic acid

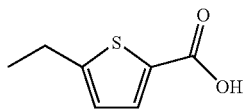

A solution of thiophencarboxylic acid (4.00 g, 30.9 mmol) in THF (24 mL) is added dropwise via a syringe to a stirred solution of LDA (32.5 mL, 2 M in toluene) in THF (40 mL) cooled to −78° C. The temperature of the reaction is maintained at −78° C. for 10 min before iodoethane (4.87 g, 30.9 mmol) is added. The mixture is stirred at −78° C. for 1 h and is then allowed to warm to rt overnight. The reaction is quenched by the addition of water. The mixture is acidified and extracted three times with diethyl ether. The org. extracts are dried over MgSO$_4$, filtered and evaporated. The crude product is purified by MPLC on reversed phase silica gel to give the title compound (1.10 g) as a brownish solid; LC-MS: $t_R$=0.80 min, $^1$H NMR (CDCl$_3$): δ 1.34 (t, J=7.3 Hz, 3H), 2.90 (q, J=7.6 Hz, 2H), 6.84 (d, J=3.5 Hz, 1H), 7.73 (d, J=3.8 Hz, 1H).

5-n-Propyl-thiophene-2-carboxylic acid

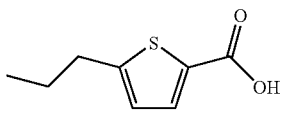

The title compound is prepared in analogy to 5-ethyl-thiophene-2-carboxylic acid starting from 2-thiophenecarboxylic acid and 1-iodopropane; LC-MS: $t_R$=0.87 min, $^1$H NMR (CDCl$_3$): δ 0.99 (t, J=7.0 Hz, 3H), 1.74 (hex, J=7.3 Hz, 2H), 2.83 (t, J=7.6 Hz, 2H), 6.82 (d, J=3.5 Hz, 1H), 7.73 (d, J=3.8 Hz, 1H).

5-n-Butyl-thiophene-2-carboxylic acid

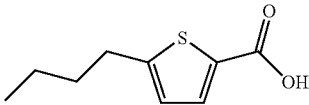

The title compound is prepared in analogy to 5-ethyl-thiophene-2-carboxylic acid starting from 2-thiophenecarboxylic acid and 1-iodobutane; LC-MS: $t_R$=0.92 min.

5-Isobutyl-thiophene-2-carboxylic acid

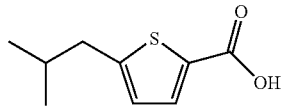

To a solution of 2-thiophene-carboxylic acid (4.16 g, 32.1 mmol) in THF (200 mL) tert. butyllithium (49 mL, 1.7 M solution in pentane, 83.6 mmol) is slowly added at −78° C. The mixture is stirred at −78° C. for 30 min before isobutyl-bromide (22.7 g, 160.7 mmol) is carefully added. The mixture is stirred at −78° C. for 5 h, then at rt for 16 h. The reaction is quenched by the addition of water (400 mL). The mixture is acidified and extracted with EA. The org. extract is dried over MgSO$_4$, filtered and evaporated. The crude product is purified by MPLC on reverse phase silica gel to give the title compound (1.67 g) as a brownish oil; LC-MS: $t_R$=0.91 min, $^1$H NMR (CDCl$_3$): δ 0.96 (d, J=6.7 Hz, 6H), 1.94 (hept, J=6.7 Hz, 1H), 2.72 (d, J=7.0 Hz, 2H), 6.80 (d, J=3.8 Hz, 1H), 7.73 (d, J=3.8 Hz, 1H).

5-(2-methyl-propenyl)-4-methyl-thiophene-2-carboxylic acid

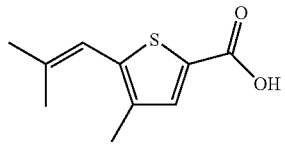

a) To a solution of methyl 5-bromo-4-methyl-thiophene-2-carboxylate (3.65 g, 15.53 mmol) in DME (30 mL), 2,4,6-tris-(2-methyl-propenyl)-cyclotriboroxane ((5.04 g, 15.53 mmol) F. Kerins, D. F. O'Shea, J. Org. Chem. 67 (2002), 4968-4971) followed by 2 M aq. K$_2$CO$_3$ (12 mL) is added. The solution is degassed and put under argon before Pd(PPh$_3$)$_4$ (366 mg, 0.317 mmol) is added. The mixture is stirred at 80° C. for 10 h before it is cooled to rt, diluted with diethyl ether (50 mL) and washed with sat. aq. NaHCO$_3$-solution (2×30 mL). The org. extract is dried over MgSO$_4$, filtered and concentrated to give 4-methyl-5-(2-methyl-propenyl)-thiophene-2-carboxylic acid methyl ester (4.08 g) as a yellow oil; LC-MS: $t_R$=1.04 min, [M+1]$^+$=211.04.

b) A solution of 4-methyl-5-(2-methyl-propenyl)-thiophene-2-carboxylic acid methyl ester (4.08 g, 19.4 mmol) in methanol (33 mL) is treated with 2 N aq. LiOH solution (10 mL). The mixture is stirred at rt for 2 h, then at 45° C. for 3 h. The reaction mixture is diluted with diethyl ether. The org. layer is separated and extracted with water. The combined aq. phase is acidified with 1 M aq. HCl, and extracted twice with diethyl ether. The combined second org. extracts are dried over MgSO$_4$, filtered and concentrated to give 4-methyl-5-(2-methyl-propenyl)-thiophene-2-carboxylic acid (3.05 g) as an off-white solid; LC-MS: $t_R$=0.92 min, [M+1]$^+$=196.98.

1-(5-Isobutyl-thiophen-2-yl)-ethanone

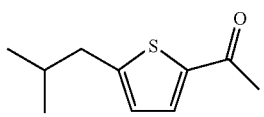

To a solution of 5-isobutyl-thiophene-2-carboxylic acid (550 mg, 2.99 mmol) in diethyl ether (20 mL), a solution of methyl lithium (3.75 mL, 1.6 M in diethyl ether) is slowly added at rt. The reaction mixture is stirred at rt for 1 h before it is carefully washed twice with water, dried over MgSO$_4$, filtered and evaporated to give the title compound (336 mg) as a slightly yellow oil, LC-MS: $t_R$=0.91 min, [M+1]$^+$=183.07.

4,N-Dihydroxy-3,5-dimethyl-benzamidine

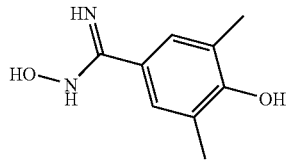

The title compound is prepared from commercially available 4-hydroxy-3,5-dimethyl-benzonitrile according to literature procedures (e.g. E. Meyer, A. C. Joussef, H. Gallardo, *Synthesis* 2003, 899-905); $^1$H NMR (CD$_3$OD): δ 7.20 (s, 2H), 2.20 (s, 6H).

4-Allyloxy-N-hydroxy-3,5-dimethyl-benzamidine

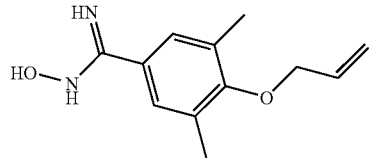

The title compound is prepared by allylating commercially available 4-hydroxy-3,5-dimethyl-benzonitrile with allylbromide in the presence of NaOH in isopropanol at rt. The nitrile is then transformed to the hydroxyamidine according to literature procedures (e.g. E. Meyer, A. C. Joussef, H. Gallardo, *Synthesis* 2003, 899-905); $^1$H NMR (CD$_3$OD): δ 7.27 (s, 2H), 6.10 (m, 1H), 5.42 (m, 1H), 5.26 (m, 1H), 4.31 (dt, J=5.6, 1.5 Hz, 2H), 2.29 (s, 6H).

3-Ethyl-4,N-dihydroxy-5-methyl-benzamidine

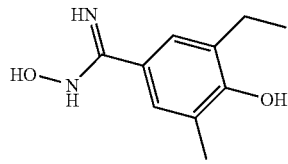

The title compound is prepared from commercially available 2-ethyl-6-methyl-phenol following literature procedures (G. Trapani, A. Latrofa, M. Franco, C. Altomare, E. Sanna, M. Usala, G. Biggio, G. Liso, *J. Med. Chem.* 41 (1998) 1846-1854; A. K. Chakraborti, G. Kaur, *Tetrahedron* 55 (1999) 13265-13268; E. Meyer, A. C. Joussef, H. Gallardo, *Synthesis* 2003, 899-905); LC-MS: $t_R$=0.55 min; $^1$H NMR (D$_6$-DMSO): δ 9.25 (s br, 1H), 7.21 (s, 2H), 5.56 (s, 2H), 2.55 (q, J=7.6 Hz, 2H), 2.15 (s, 3H), 1.10 (t, J=7.6 Hz, 3H).

4-Allyloxy-3-ethyl-N-hydroxy-5-methyl-benzamidine

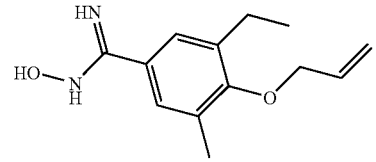

The title compound is prepared by allylating 3-ethyl-4-hydroxy-5-methyl-benzaldehyde which is prepared from 2-ethyl-6-methyl-phenol following literature procedures (see 3-ethyl-4,N-dihydroxy-5-methyl-benzamidine). The aldehyde is then transformed into the corresponding hydroxyamidine according to literature procedures (see 3-ethyl-4,N-dihydroxy-5-methyl-benzamidine); LC-MS: $t_R$=0.72 min, [M+1]$^+$=235.09; $^1$H NMR (CD$_3$OD): δ 7.31 (s, 1H), 7.29 (s, 1H), 6.10 (m, 1H), 5.43 (dd, J=17.0, 1.5 Hz, 1H), 5.27 (dd, J=10.3, 1.2 Hz, 1H), 4.81 (s br, 3H), 4.31 (d, J=5.6 Hz, 2H), 2.67 (q, J=7.6 Hz, 2H), 2.30 (s, 3H), 1.23 (t, J=7.6 Hz, 4H).

3,5-Diethyl-4,N-dihydroxy-benzamidine

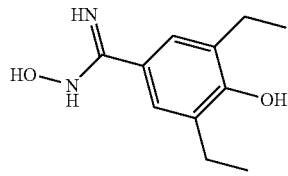

The title compound is prepared from commercially available 2,6-diethylaniline following literature procedures (G. G. Ecke, J. P. Napolitano, A. H. Filbey, A. J. Kolka, *J. Org. Chem.*

22 (1957) 639-642; and literature cited for 3-ethyl-4,N-dihydroxy-5-methyl-benzamidine).

4-Allyloxy-N-hydroxy-2-methoxy-benzamidine

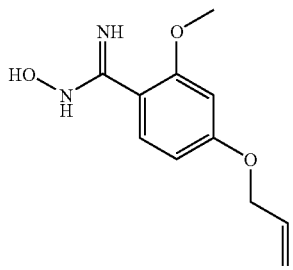

The title compound is prepared from commercially available 4-hydroxy-2-methoxy-benzaldehyde following literature procedures (references cited for 3-ethyl-4,N-dihydroxy-5-methyl-benzamidine); LC-MS: $t_R$=0.64 min; $[M+1]^+$=223.24; $^1$H NMR (D$_6$-DMSO): δ 9.33 (s br, 1H), 7.30 (d, J=8.2 Hz, 1H), 6.60 (d, J=2.3 Hz, 1H), 6.50 (dd, J=2.3, 8.2 Hz, 1H), 6.10-5.94 (m, 1H), 5.50 (s, 2H), 5.40 (d, J=17.0 Hz, 1H), 5.24 (d, J=10.6 Hz, 1H), 4.57 (d, J=4.7 Hz, 2H), 3.76 (s, 3H).

4-Allyloxy-3,5-dimethyl-benzoic acid hydrazide

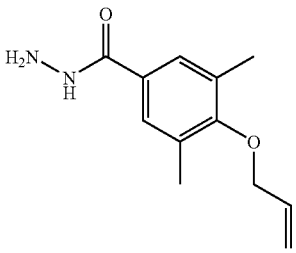

a) A mixture of 4-bromo-2,6-dimethyl-phenol (20.1 g, 100 mmol) and allylchloride (32.7 g, 428 mmol) in 3 N aq. NaOH (100 mL) and isopropanol (250 mL) is stirred at 60° C. for 15 h before it is diluted with 1 N aq. NaOH (100 mL). The mixture is extracted with diethyl ether (300 mL, 150 mL) and the combined org. extracts are washed with 1 N aq. NaOH (2×100 mL), 1 M aq. NaH$_2$PO$_4$ (50 mL), dried over Na$_2$SO$_4$, filtered and concentrated to give 2-allyloxy-5-bromo-1,3-dimethyl-benzene (23.6 g) as a yellow oil, LC-MS: $t_R$=1.08 min, $[M+1]^+$=241.20.

b) To a solution of 2-allyloxy-5-bromo-1,3-dimethyl-benzene (23.6 g, 98.0 mmol) in THF (150 mL) is added at –75° C. a solution of n-BuLi (90 mL, 1.5 M in diethyl ether). The temperature remains at –75° C. The mixture is stirred for 30 min and then transferred via double-tip canula into a cooled (0° C.) solution of dimethylcarbonate (21.4 g, 238 mmol) in THF (90 mL). The mixture is stirred for 2 h at 0° C., then warmed to rt during 15 h. The solvent of the mixture is evaporated and re-evaporated from EtOH (200 mL) to remove most of the butylacetate side product. The mixture is taken up in 2 N aq. LiOH (150 mL) and EtOH (200 mL) and stirred at rt for 2 h, then at 60° C. for 1 h. The EtOH is evaporated and the remaining mixture is diluted with 0.5 N aq. NaOH and extracted with diethyl ether (200 mL). The org. extract is washed with 1M aq. NaOH (5×50 mL) and the combined aq. washings are re-extracted with ether (100 mL). The aq. phase is acidified with 25% aq. HCl and extracted with DCM (5×50 mL). The combined org. extracts are dried over Na$_2$SO$_4$, filtered, evaporated and dried in vacuo at 60° C. for 15 h to give 4-allyloxy-3,5-dimethyl-benzoic acid (8.0) as yellow-brown solid. LC-MS: $t_R$=0.90 min.

c) To a solution of 4-allyloxy-3,5-dimethyl-benzoic acid (5.26 g, 25.5 mmol) in CHCl$_3$ (75 mL), thionylchloride (7.5 mL, 103 mmol) is added at rt. The mixture is refluxed for 2 h before the solvent is evaporated to give crude 4-allyloxy-3,5-dimethyl-benzoic acid chloride as a brownish oil. To a solution of the acid chloride in DCM (50 mL), hydrazine (75 mL of a 1 M solution in THF) in DCM (250 mL) is added at 0° C. The mixture is stirred at rt for 15 h before it is diluted with diethyl ether and extracted with 1 N aq. HCl (75 mL, then 5×50 mL). The combined aq. extracts are basified by adding 33% aq. KOH solution and extracted with DCM (5×50 mL). The combined DCM extracts are dried over Na$_2$SO$_4$, filtered and evaporated to give 4-allyloxy-3,5-dimethyl-benzoic acid hydrazide (5.39 g) as a white solid; LC-MS: $t_R$=0.71 min; $[M+1]^+$=221.20; $^1$H NMR (D$_6$-DMSO): δ 2.22 (s, 6H), 4.28-4.37 (m, 2H), 4.39 (s, 2H), 5.19-5.28 (m, 1H), 5.36-5.47 (m, 1H), 6.00-6.15 (m, 1H), 7.49 (s, 2H), 9.55 (s, 1H).

4-Benzyloxy-3,5-dimethyl-benzoic acid hydrazide

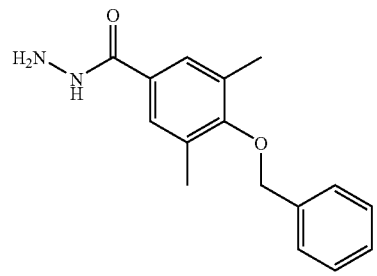

4-Benzyloxy-3,5-dimethyl-benzoic acid hydrazide is prepared in analogy to 4-allyloxy-3,5-dimethyl-benzoic acid hydrazide starting from 4-benzyloxy-3,5-dimethylbenzoic acid; LC-MS: $t_R$=0.81 min; $[M+1]^+$=271.41.

4-Benzyloxy-3-ethyl-5-methyl-benzoic acid hydrazide

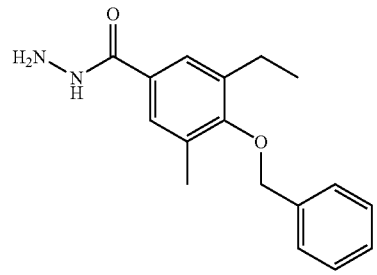

a) To a solution of 3-ethyl-4-hydroxy-5-methyl-benzaldehyde (34.9 g, 0.213 mol, prepared from 2-ethyl-6-methyl-phenol according to the literature cited for 3-ethyl-4,N-dihydroxy-5-methyl-benzamidine) in acetonitrile (350 mL), K$_2$CO$_3$ (58.7 g, 0.425 mol) and benzylbromide (36.4 g, 0.213 mol) is added. The mixture is stirred at 60° C. for 2 h before it is cooled to rt, diluted with water and extracted twice with EA. The org. extracts are washed with water and concentrated to give crude 4-benzyloxy-3-ethyl-5-methyl-benzaldehyde (45 g) as an orange oil. $^1$H NMR (CDCl$_3$): δ 1.29 (t, J=7.5 Hz, 3H), 2.40 (s, 3H), 2.77 (q, J=7.8 Hz, 2H), 4.90 (s, 2H), 7.31-7.52 (m, 5H), 7.62 (d, J=1.5 Hz, 1H), 7.66 (d, J=1.8 Hz, 1H), 9.94 (s, 1H).

b) To a mixture of 4-benzyloxy-3-ethyl-5-methyl-benzaldehyde (132 g, 0.519 mol) and 2-methyl-2-butene (364 g, 5.19 mol) in tert.-butanol (1500 mL), a solution of NaH$_2$PO$_4$ dihydrate (249 g, 2.08 mol) in water (1500 mL) is added. To this mixture, NaClO$_2$ (187.8 g, 2.08 mol) is added in portions. The temperature of the reaction mixture is kept below 30° C., and evolution of gas is observed. Upon completion of the addition, the orange bi-phasic mixture is stirred well for 3 h before it is diluted with TBME (1500 mL). The org. layer is separated and washed with 20% aq. NaHS solution (1500 mL) and water (500 mL). The org. phase is then extracted three times with 0.5 N aq. NaOH (1000 mL), the aqueous phase is acidified with 25% aq. HCl (500 mL) and extracted twice with TBME (1000 mL). These org. extracts are combined and evaporated to dryness to give 4-benzyloxy-3-ethyl-5-methyl-benzoic acid; $^1$H NMR (D$_6$-DMSO): δ 1.17 (t, J=7.5 Hz, 3H), 2.31 (s, 3H), 2.67 (q, J=7.5 Hz, 2H), 4.86 (s, 2H), 7.34-7.53 (m, 5H), 7.68 (s, 2H), 12.70 (s, 1H).

c) 4-Benzyloxy-3-ethyl-5-methyl-benzoic acid is converted to 4-benzyloxy-3-ethyl-5-methyl-benzoic acid hydrazide following step c) of the preparation of 4-allyloxy-3,5-dimethyl-benzoic acid hydrazide; LC-MS: $t_R$=0.82 min, [M+1]$^+$=285.44.

Methanesulfonic acid
2,2-dimethyl-[1,3]dioxan-5-ylmethyl ester

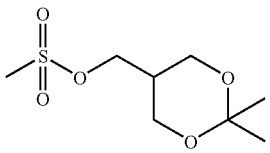

The title compound is prepared following the procedures given in B. Xu, A. Stephens, G. Kirschenheuter, A. F. Greslin, X. Cheng, J. Sennelo, M. Cattaneo, M. L. Zighetti, A. Chen, S.-A. Kim, H. S. Kim, N. Bischofberger, G. Cook, K. A. Jacobson, *J. Med. Chem.* 45 (2002) 5694-5709.

Example 1

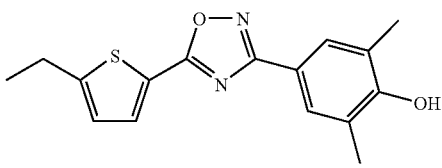

a) To a solution of 5-ethyl-thiophene-2-carboxylic acid (502 mg, 3.21 mmol) and DIPEA (1.04 g, 8.03 mmol) in DCM (16 mL), TBTU (1.13 g, 3.53 mmol) is added at 0° C. The mixture is stirred at 0° C. for 1 h before the reaction is quenched with water (2 mL). The DCM is evaporated and the remaining residue is diluted with EA, washed with sat. aq. NaHCO$_3$ solution and water, dried over MgSO$_4$, filtered and evaporated. The crude product was purified by crystallisation from acetonitrile to give 5-ethyl-thiophene-2-carboxylic acid (4,N-dihydroxy-3,5-dimethyl-benzamidine) ester (600 mg) as a white solid; LC-MS: $t_R$=0.94 min, [M+1]$^+$=319.02.

b) A solution of 5-ethyl-thiophene-2-carboxylic acid (4,N-dihydroxy-3,5-dimethyl-benzamidine) ester (600 mg, 1.88 mmol) in dioxane (40 mL) is stirred at 100° C. for 18 h. The solvent is evaporated and the residue is separated by CC on silica gel eluting with heptane:EA 4:1 to give 4-[5-(5-ethyl-thiophen-2-yl)-[1,2,4]oxadiazol-3-yl]-2,6-dimethyl-phenol (525 mg) as a pale yellow oil; LC-MS: $t_R$=1.09 min, [M+1]$^+$=301.11.

Example 2

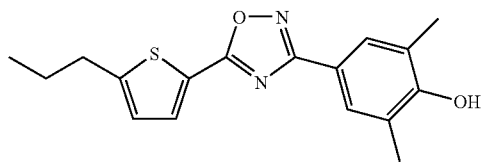

2,6-Dimethyl-4-[5-(5-propyl-thiophen-2-yl)-[1,2,4]oxadiazol-3-yl]-phenol is prepared in analogy to Example 1; LC-MS: $t_R$=1.10 min, [M+1]$^+$=315.35.

Example 3

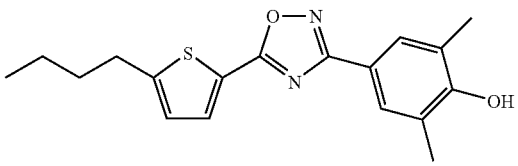

4-[5-(5-Butyl-thiophen-2-yl)-[1,2,4]oxadiazol-3-yl]-2,6-dimethyl-phenol is prepared in analogy to Example 1; LC-MS: $t_R$=1.15 min, [M+1]$^+$=329.15.

Example 4

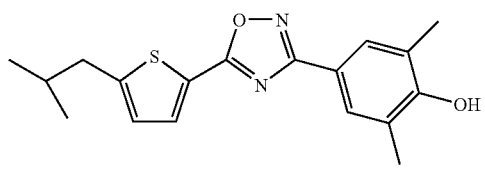

4-[5-(5-Isobutyl-thiophen-2-yl)-[1,2,4]oxadiazol-3-yl]-2,6-dimethyl-phenol is prepared in analogy to Example 1; LC-MS: $t_R$=1.15 min, [M+1]$^+$=329.09.

Example 5

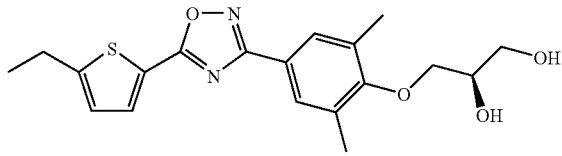

To a solution of 4-[5-(5-ethyl-thiophen-2-yl)-[1,2,4]oxadiazol-3-yl]-2,6-dimethyl-phenol (79 mg, 0.263 mmol) in isopropanol (3 mL) and 3 N aq. NaOH (0.6 mL), (R)-3-chloro-propane-1,2-diol (148 mg, 1.31 mmol) is added. The mixture is stirred at rt for 2 h, then at 65° C. for 16 h before another portion of (R)-3-chloro-propane-1,2-diol (119 mg, 1.05 mmol) is added. Stirring is continued at 65° C. for 24 h. The reaction mixture is diluted with water and extracted with diethyl ether. The org. extract is dried over MgSO$_4$, filtered and evaporated. The crude product is purified by chromatography on prep. TLC plates with DCM containing 4% of 7 N NH$_3$ in methanol to give (2R)-3-{4-[5-(5-ethyl-thiophen-2-yl)-[1,2,4]oxadiazol-3-yl]-2,6-dimethyl-phenoxy}-propane-1,2-diol as an off-white solid; LC-MS: $t_R$=0.99 min; [M+1]$^+$=375.13; $^1$H NMR (CDCl$_3$): δ 7.83 (s, 2H), 7.80 (d, J=3.8 Hz, 1H), 6.93 (d, J=3.8 Hz, 1H), 4.20-4.11 (m, 1H), 3.97-3.93 (m, 1H), 3.91 (dd, J=11.5, 4.3 Hz, 1H), 3.85 (dd, J=11.5, 5.5 Hz, 1H), 2.97 (q, J=7.5 Hz, 2H), 2.39 (s, 6H), 1.41 (t, J=7.5 Hz, 3H).

Examples 6 To 12

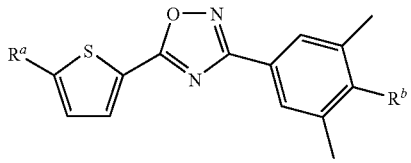

The following Examples are prepared in analogy to Example 5 starting from the Examples indicated using either (R)- or (S)-3-chloro-propane-1,2-diol:

| Example | starting from Example | R$^a$ | R$^b$ | LC-MS $t_R$ (min) | [M + H]$^+$ |
|---|---|---|---|---|---|
| 6 | 1 | ethyl | O—CH$_2$—CH(OH)—CH$_2$OH (S) | 0.99 | 375.01 |
| 7 | 2 | n-propyl | O—CH$_2$—CH(OH)—CH$_2$OH (R) | 1.03 | 389.20 |
| 8 | 2 | n-propyl | O—CH$_2$—CH(OH)—CH$_2$OH (S) | 1.00 | 389.38 |
| 9 | 3 | n-butyl | O—CH$_2$—CH(OH)—CH$_2$OH (R) | 1.04 | 403.40 |
| 10 | 3 | n-butyl | O—CH$_2$—CH(OH)—CH$_2$OH (S) | 1.06 | 403.11 |
| 11 | 4 | isobutyl | O—CH$_2$—CH(OH)—CH$_2$OH (R) | 1.03 | 403.40 |
| 12 | 4 | isobutyl | O—CH$_2$—CH(OH)—CH$_2$OH (S) | 1.06 | 403.05 |

Example 12

$^1$H NMR(CDCl$_3$): δ 0.98 (d, J=6.4 Hz, 6H), 1.96 (hept, J=6.5 Hz, 1H), 2.35 (s, 6H), 2.76 (d, J=7.0 Hz, 2H), 3.76-3.94 (m, 4H), 4.09-4.18 (m, 1H), 6.86 (d, J=3.5 Hz, 1H), 7.77 (d, J=3.5 Hz, 1H), 7.80 (s, 2H).

Example 13

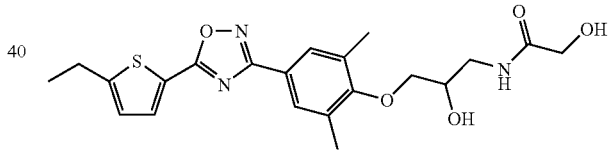

a) A mixture of 4-[5-(5-ethyl-thiophen-2-yl)-[1,2,4]oxadiazol-3-yl]-2,6-dimethyl-phenol (367 mg, 1.22 mmol) and epichlorohydrine (565 mg, 6.10 mmol) in isopropanol (20 mL) and 3 N aq. NaOH (6 mL) is stirred at 40° C. for 15 h. The mixture is diluted with diethyl ether, washed with sat. aq. NaHCO$_3$ and water, dried over MgSO$_4$, filtered and evaporated. The crude product is purified by CC on silica gel eluting with heptane:EA 9:1 to give 3-(3,5-dimethyl-4-oxiranylmethoxy-phenyl)-5-(5-ethyl-thiophen-2-yl)-[1,2,4]oxadiazole (123 mg) as a pale yellow oil; LC-MS: $t_R$=1.15 min, [M+1]$^+$=357.11.

b) A solution of 3-(3,5-dimethyl-4-oxiranylmethoxy-phenyl)-5-(5-ethyl-thiophen-2-yl)-[1,2,4]oxadiazole (123 mg, 0.345 mmol) in 7 N NH$_3$ in methanol (10 mL) is stirred at 45° C. for 16 h. The solvent is evaporated and the residue is separated by chromatography on prep. TLC plates with DCM containing 6% of 7 N NH$_3$ in methanol to give 1-amino-3-{4-[5-(5-ethyl-thiophen-2-yl)-[1,2,4]oxadiazol-3-yl]-2,6-dimethyl-phenoxy}-propan-2-ol (35 mg) as a white solid; LC-MS: $t_R$=0.84 min, [M+1]$^+$=374.14.

c) To a cold solution (0° C.) of 1-amino-3-{4-[5-(5-ethyl-thiophen-2-yl)-[1,2,4]oxadiazol-3-yl]-2,6-dimethyl-phenoxy}-propan-2-ol (32 mg, 86 μmol) in DCM (1 mL), DIPEA (45 mg, 345 μmol), glycolic acid (13 mg, 172 μmol) and finally TBTU (33 mg, 101 μmol) is added. The mixture is stirred at rt for 1 h before it is diluted with EA and washed with water. The aq. phase is extracted back with EA. The combined org. extracts are dried over MgSO$_4$, filtered and evaporated. The crude product is purified by crystallisation from acetonitrile to give N-(3-{4-[5-(5-ethyl-thiophen-2-yl)-[1,2,4]oxadiazol-3-yl]-2,6-dimethyl-phenoxy}-2-hydroxy-propyl)-2-hydroxy-acetamide (7 mg) as a white solid; LC-MS: $t_R$=0.95 min, [M+1]$^+$=432.16.

Examples 14 To 16

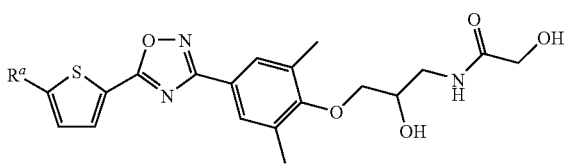

The following Examples are prepared in analogy to Example 13 starting from the Example indicated:

| Example | starting from Example | R$^a$ | LC-MS $t_R$ (min) | [M + H]$^+$ |
|---------|----------------------|-------|-------------------|-------------|
| 14 | 2 | n-propyl | 0.99 | 446.14 |
| 15 | 3 | n-butyl | 1.02 | 460.26 |
| 16 | 4 | isobutyl | 1.01 | 460.18 |

Example 15

$^1$H NMR (D$_6$-DMSO): δ 0.93 (t, J=7.3 Hz, 3H), 1.33-1.44 (m, 2H), 1.63-1.72 (m, 2 H), 2.33 (s, 6H), 2.93 (t, J=7.5 Hz, 2H), 3.20-3.30 (m, 1H), 3.37-3.48 (m, 1H), 3.69-3.80 (m, 2H), 3.84 (d, J=5.8 Hz, 2H), 3.91-3.99 (m, 1H), 5.30 (d, J=5.3 Hz, 1H), 5.56 (t, J=5.8 Hz, 1H), 7.12 (d, J=3.8 Hz, 1H), 7.69 (t, J=6.0 Hz, 1H), 7.72 (s, 2H), 7.90 (d, J=3.5 Hz, 1H).

Example 16

$^1$H NMR (D$_6$-DMSO): δ 0.92 (d, J=6.4 Hz, 5H), 1.83-2.00 (m, 1H), 2.30 (s, 6H), 2.78 (d, J=7.0 Hz, 2H), 3.14-3.27 (m, 2H), 3.36-3.48 (m, 2H), 3.65-3.78 (m, 2H), 3.81 (d, J=5.6 Hz, 2H), 3.87-3.99 (m, 1H), 5.26 (d, J=5.0 Hz, 1H), 5.52 (t, J=5.6 Hz, 1H), 7.07 (d, J=3.5 Hz, 1H), 7.66 (m, 3H), 7.89 (d, J=3.5 Hz, 1H).

Example 17

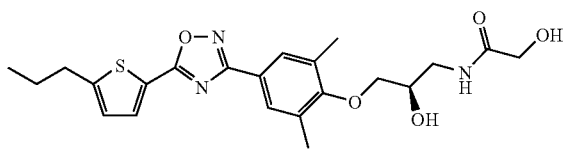

(2R)—N-(3-{2,6-Dimethyl-4-[5-(5-propyl-thiophen-2-yl)-[1,2,4]oxadiazol-3-yl]-phenoxy}-2-hydroxy-propyl)-2-hydroxy-acetamide is prepared in analogy to Example 13 starting from Example 2 and using (R)-2-chloromethyl-oxirane as the alkylating agent; LC-MS: $t_R$=0.98 min, [M+1]$^+$=446.20.

Example 18

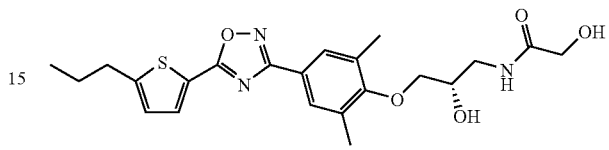

(2S)—N-(3-{2,6-Dimethyl-4-[5-(5-propyl-thiophen-2-yl)-[1,2,4]oxadiazol-3-yl]-phenoxy}-2-hydroxy-propyl)-2-hydroxy-acetamide is prepared in analogy to Example 13 starting from Example 2 and using (S)-2-chloromethyl-oxirane as the alkylating agent; LC-MS: $t_R$=0.98 min, [M+1]$^+$=446.19, $^1$H NMR (CDCl$_3$): δ 1.04 (t, J=7.3 Hz, 3H), 1.72-1.84 (m, 2H), 2.36 (s, 6H), 2.89 (t, J=7.5 Hz, 2H), 3.19 (s br, 1H), 3.47-3.56 (m, 1H), 3.60 (s br, 1H), 3.73-3.92 (m, 3H), 4.18 (s, 2H), 6.90 (d, J=3.8 Hz, 1H), 7.12 (t, J=5.8 Hz, 1H), 7.78 (d, J=3.8 Hz, 1H), 7.80 (s, 2H).

Example 19

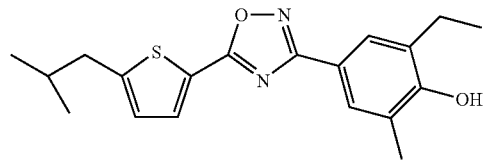

2-Ethyl-4-[5-(5-isobutyl-thiophen-2-yl)-[1,2,4]oxadiazol-3-yl]-6-methyl-phenol is prepared in analogy to Example 1 using 3-ethyl-4,N-dihydroxy-5-methyl-benzamidine; LC-MS: $t_R$=1.16 min, [M+1]$^+$=343.02.

Example 20

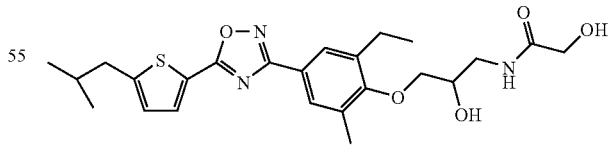

N-(3-{2-Ethyl-4-[5-(5-isobutyl-thiophen-2-yl)-[1,2,4]oxadiazol-3-yl]-6-methyl-phenoxy}-2-hydroxy-propyl)-2-hydroxy-acetamide is prepared in analogy to Example 13 starting from Example 19; LC-MS: $t_R$=1.01 min; $^1$H NMR (CDCl$_3$): δ 0.99 (d, J=6.7 Hz, 3H), 1.29 (t, J=7.6 Hz, 3H), 1.90-2.05 (m, 1H), 2.35 (s, 3H), 2.57 (s br, 1H), 2.67-2.80 (m, 4H), 3.23 (s br, 1H), 3.44-3.56 (m, 1H), 3.72-3.92 (m, 3H), 4.14-4.22 (m, 3H), 6.87 (d, J=3.5 Hz, 1H), 6.97 (t br, 1H), 7.78 (d, J=3.8 Hz, 1H), 7.82 (s, 1H), 7.84 (s, 1H).

Example 21

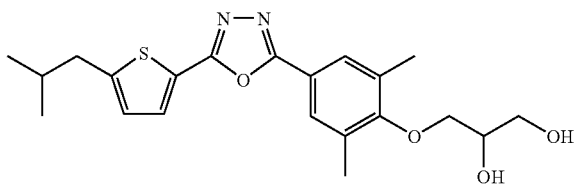

a) To a solution of 5-isobutyl-thiophene-2-carboxylic acid (830 mg, 4.51 mmol) and DIPEA (680 mg, 5.27 mmol) in DCM (20 mL) is added TBTU (1.59 g, 4.96 mmol) at rt. The mixture is stirred at rt for 45 min before 4-allyloxy-3,5-dimethyl-benzoic acid hydrazide (993 mg, 4.50 mmol) is added. Stirring is continued for 2 h. The mixture is diluted with ether (200 mL) and washed with 1M aq. HCl (3×50 mL), 1M aq. NaOH (3×50 mL) and brine (50 mL). The org. extract is dried over MgSO$_4$, filtered and evaporated to give the crude 4-allyloxy-3,5-dimethyl-benzoic acid N'-(5-isobutyl-thiophene-2-carbonyl)-hydrazide (1.40 g) as a yellow oil that slowly solidifies; LC-MS: $t_R$=1.02 min, [M+1]$^+$=387.10.

b) A solution of 4-allyloxy-3,5-dimethyl-benzoic acid N'-(5-isobutyl-thiophene-2-carbonyl)-hydrazide (1.40 g, 3.62 mmol) and Burgess reagent (1.12 g, 4.71 mmol) in THF (15 mL) is stirred at 110° C. for 3 min under microwave irradiation. The mixture is diluted with diethyl ether, washed with water, dried over MgSO$_4$, filtered and evaporated. The crude product is purified by CC on silica gel eluting with heptane:EA 9:1 to give 2-(4-allyloxy-3,5-dimethyl-phenyl)-5-(5-isobutyl-thiophen-2-yl)-[1,3,4]oxadiazole (1.02 g) as a colourless oil; LC-MS: $t_R$=1.21 min, [M+1]$^+$=369.15.

c) To a solution of 2-(4-allyloxy-3,5-dimethyl-phenyl)-5-(5-isobutyl-thiophen-2-yl)-[1,3,4]oxadiazole (1.02 g, 2.77 mmol) in acetone (24 mL) and water (2.4 mL), NMO (1.85 g, 13.7 mmol) and OsO$_4$ (128 mg, 13 µmol, as a 2.5% solution in butanol) is added. The mixture is stirred at rt for 16 h before it is diluted with water (50 mL) and extracted with EA (2×100 mL). The combined org. extracts are dried over Na$_2$SO$_4$, filtered and evaporated. The crude product is purified by CC on silica gel eluting with EA to give 3-{4-[5-(5-isobutyl-thiophen-2-yl)-[1,3,4]oxadiazol-2-yl]-2,6-dimethyl-phenoxy}-propane-1,2-diol (680 mg) as a colourless oil; LC-MS: $t_R$=0.99 min, [M+1]$^+$=403.14.

Example 22

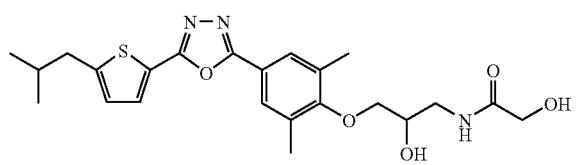

a) To a solution of 3-{4-[5-(5-isobutyl-thiophen-2-yl)-[1,3,4]oxadiazol-2-yl]-2,6-dimethyl-phenoxy}-propane-1,2-diol (627 mg, 1.56 mmol) and DIPEA (311 mg, 2.41 mmol) in DCM (10 mL), methanesulfonyl chloride (207 mg, 1.81 mmol) is added. The mixture is stirred at rt before another portion of DIPEA (40 mg, 0.31 mmol) and methanesulfonyl chloride (36 mg, 0.31 mmol) is added. Stirring is continued for 1 h before the reaction is quenched by adding water. The mixture is extracted with DCM. The org. extract is washed with water, dried over MgSO$_4$, filtered and evaporated. The crude product is purified by CC on silica gel eluting with heptane:EA 7:3 to give methanesulfonic acid 2-hydroxy-3-{4-[5-(5-isobutyl-thiophen-2-yl)-[1,3,4]oxadiazol-2-yl]-2,6-dimethyl-phenoxy}-propyl ester (220 mg) as a colourless oil; LC-MS: $t_R$=1.08 min, [M+1]$^+$=481.09.

b) A solution of methanesulfonic acid 2-hydroxy-3-{4-[5-(5-isobutyl-thiophen-2-yl)-[1,3,4]oxadiazol-2-yl]-2,6-dimethyl-phenoxy}-propyl ester (220 mg, 0.458 mmol) in THF (10 mL) and 7 N NH$_3$ in methanol (10 mL) is stirred at 65° C. for 15 h. The solvent is evaporated and the residue is separated by chromatography on prep. TLC plates with DCM containing 6% of 7 N NH$_3$ in methanol to give 1-amino-3-{4-[5-(5-isobutyl-thiophen-2-yl)-[1,3,4]oxadiazol-2-yl]-2,6-dimethyl-phenoxy}-propan-2-ol (110 mg) as a yellow oil; LC-MS: $t_R$=0.83 min, [M+1]$^+$=402.48.

c) To a solution of 1-amino-3-{4-[5-(5-isobutyl-thiophen-2-yl)-[1,3,4]oxadiazol-2-yl]-2,6-dimethyl-phenoxy}-propan-2-ol (109 mg, 271 µmol) in DCM (10 mL), DIPEA (140 mg, 1.086 mmol) and glycolic acid (41 mg, 543 µmol) followed by TBTU (102 mg, 319 µmol) is added at 0° C. The mixture is stirred at rt for 1 h before it is diluted with EA and washed with water. The water phase is separated and extracted once more with EA. The combined org. extracts are dried over MgSO$_4$, filtered and evaporated. The crude product is purified by chromatography on prep. TLC plates with DCM containing 4% of 7 N NH$_3$ in methanol to give 2-hydroxy-N-(2-hydroxy-3-{4-[5-(5-isobutyl-thiophen-2-yl)-[1,3,4]oxadiazol-2-yl]-2,6-dimethyl-phenoxy}-propyl)-acetamide (31 mg) as a white solid; LC-MS: $t_R$=0.94 min, [M+1]$^+$=460.51.

Example 23

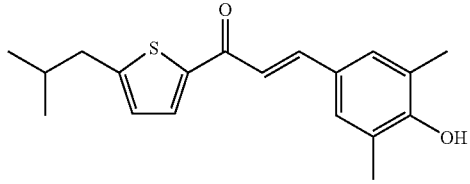

To a solution of 1-(5-isobutyl-thiophen-2-yl)-ethanone (336 mg, 1.84 mmol) and 3,5-dimethyl-4-hydroxy-benzaldehyde (277 mg, 1.84 mmol) in EtOH (6 mL), 5 N HCl in isopropanol (2.5 mL) is added. The dark solution is stirred at rt for 6 h before the solvent is removed in vacuo. The residue is dissolved in EA (80 mL) and washed with sat. aq. NaHCO$_3$ solution (25 mL) and brine. The washings are extracted back with EA. The combined org. extracts are dried over MgSO$_4$, filtered and evaporated to give 3-(4-hydroxy-3,5-dimethylphenyl)-1-(5-isobutyl-thiophen-2-yl)-propenone (682 mg) as a yellow powder; LC-MS: $t_R$=1.10 min, [M+1]$^+$=315.15.

Example 24

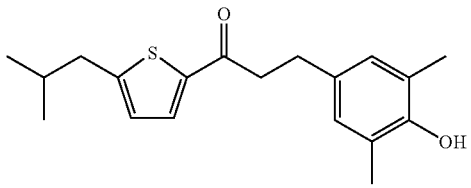

To a solution of 3-(4-hydroxy-3,5-dimethyl-phenyl)-1-(5-isobutyl-thiophen-2-yl)-propenone (660 mg) in THF (10 mL) and EtOH (5 mL), Pd/C (150 mg, 10% Pd) is added and the suspension is stirred at rt under 5 bar of $H_2$ for 23 h. Another portion of Pd/C (150 mg) is added and stirring is continued at rt under 5 bar of $H_2$ for 8 h. The catalyst is filtered off and the filtrate is evaporated to give 3-(4-hydroxy-3,5-dimethyl-phenyl)-1-(5-isobutyl-thiophen-2-yl)-propan-1-one (554 mg) as an orange oil; LC-MS: $t_R$=1.10 min, [M+1]$^+$=317.04.

Example 25

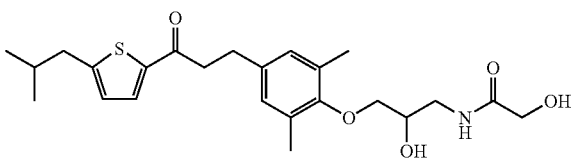

2-Hydroxy-N-(2-hydroxy-3-{4-[3-(5-isobutyl-thiophen-2-yl)-3-oxo-propyl]-2,6-dimethyl-phenoxy}-propyl)-acetamide is prepared from Example 24 in analogy to Example 13; LC-MS: $t_R$=0.97 min, [M+1]$^+$=448.21.

Example 26

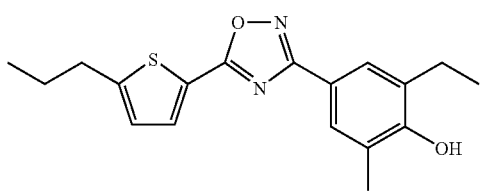

2-Ethyl-6-methyl-4-[5-(5-propyl-thiophen-2-yl)-[1,2,4]oxadiazol-3-yl]-phenol is prepared in analogy to Example 1 starting from 5-propyl-thiophene-2-carboxylic acid and 3-ethyl-4,N-dihydroxy-5-methyl-benzamidine; LC-MS: $t_R$=1.12 min, [M+1]$^+$=329.14.

Example 27

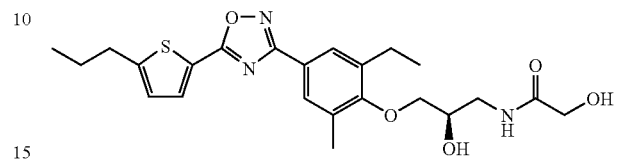

(2R)—N-(3-{2-Ethyl-6-methyl-4-[5-(5-propyl-thiophen-2-yl)-[1,2,4]oxadiazol-3-yl]-phenoxy}-2-hydroxy-propyl)-2-hydroxy-acetamide is prepared in analogy to Example 13 starting from Example 26; LC-MS: $t_R$=0.95 min, [M+1]$^+$=460.15.

Example 28

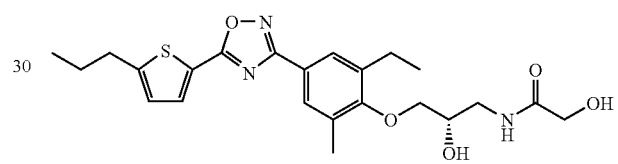

(2S)—N-(3-{2-Ethyl-6-methyl-4-[5-(5-propyl-thiophen-2-yl)-[1,2,4]oxadiazol-3-yl]-phenoxy}-2-hydroxy-propyl)-2-hydroxy-acetamide is prepared in analogy to Example 13 starting from Example 26; LC-MS: $t_R$=0.95 min, [M+1]$^+$=460.13.

Example 29

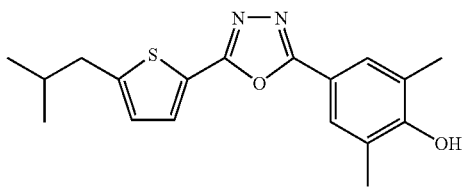

2-(4-Benzyloxy-3,5-dimethyl-phenyl)-5-(5-isobutyl-thiophen-2-yl)-[1,3,4]oxadiazole is prepared in analogy to Example 21 step a) and b) by coupling and cyclising 5-isobutyl-thiophene-2-carboxylic acid with 4-benzyloxy-3,5-dimethyl-benzoic acid hydrazide, LC-MS: $t_R$=1.06 min, [M+1]$^+$=437.17. To a solution of this compound (2.83 g, 6.75 mmol) in EtOH (50 mL) and THF (50 mL) is added Pd/C (10% Pd, 400 mg) and the slurry is stirred at rt for 48 h under 5 bar of $H_2$. The mixture is filtered, the filtrate is concentrated and the crude product is purified by CC on silica gel eluting with heptane:EA 8:25 to give 4-[5-(5-isobutyl-thiophen-2-yl)-[1, 3,4]oxadiazol-2-yl]-2,6-dimethyl-phenol (943 mg) as a white powder; LC-MS: $t_R$=1.09 min, [M+1]$^+$=329.36.

Example 30

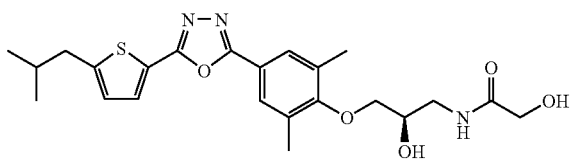

Starting from 4-[5-(5-isobutyl-thiophen-2-yl)-[1,3,4]oxadiazol-2-yl]-2,6-dimethyl-phenol, 2-hydroxy-N-((2R)-2-hydroxy-3-{4-[5-(5-isobutyl-thiophen-2-yl)-[1,3,4]oxadiazol-2-yl]-2,6-dimethyl-phenoxy}-propyl)-acetamide is prepared in analogy to Example 13; LC-MS: $t_R$=0.95 min, [M+1]$^+$= 460.18.

Example 31

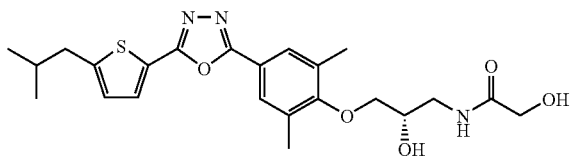

Starting from 4-[5-(5-isobutyl-thiophen-2-yl)-[1,3,4]oxadiazol-2-yl]-2,6-dimethyl-phenol, 2-hydroxy-N-((2S)-2-hydroxy-3-{4-[5-(5-isobutyl-thiophen-2-yl)-[1,3,4]oxadiazol-2-yl]-2,6-dimethyl-phenoxy}-propyl)-acetamide is prepared in analogy to Example 13; LC-MS: $t_R$=0.95 min, [M+1]$^+$= 460.18, $^1$H NMR δ 0.99 (d, J=6.5 Hz, 6H), 1.90-2.01 (m, 1H), 2.31 (s, 6H), 2.75 (d, J=7.0 Hz, 2H), 3.46-3.54 (m, 1H), 3.73-3.91 (m, 3H), 4.15-4.23 (m, 3 H), 4.26 (s br, 1 H), 4.45 (s br, 1 H), 6.84 (d, J=3.3 Hz, 1H), 7.42 (t br, J=5.5 Hz, 1H), 7.64 (d, J=3.5 Hz, 1H), 7.68 (s, 2H).

Example 32

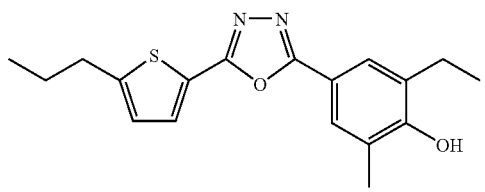

2-Ethyl-6-methyl-4-[5-(5-propyl-thiophen-2-yl)-[1,3,4]oxadiazol-2-yl]-phenol is prepared in analogy to Example 29 starting from 4-benzyloxy-3-ethyl-5-methyl-benzoic acid hydrazide and 5-propyl-thiophene-2-carboxylic acid; LC-MS: $t_R$=0.99 min, [M+1]$^+$=329.13.

Example 33

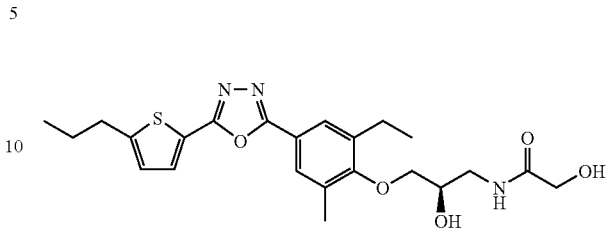

N-((2R)-3-{2-Ethyl-6-methyl-4-[5-(5-propyl-thiophen-2-yl)-[1,3,4]oxadiazol-2-yl]-phenoxy}-2-hydroxy-propyl)-2-hydroxy-acetamide is prepared in analogy to Example 13 from Example 32; LC-MS: $t_R$=0.85 min, [M+1]$^+$=460.08.

Example 34

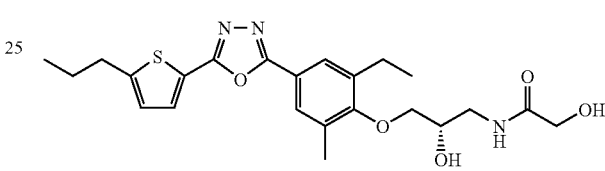

N-((2S)-3-{2-Ethyl-6-methyl-4-[5-(5-propyl-thiophen-2-yl)-[1,3,4]oxadiazol-2-yl]-phenoxy}-2-hydroxy-propyl)-2-hydroxy-acetamide is prepared in analogy to Example 13 from Example 32; LC-MS: $t_R$=0.85 min, [M+1]$^+$=460.08.

Example 35

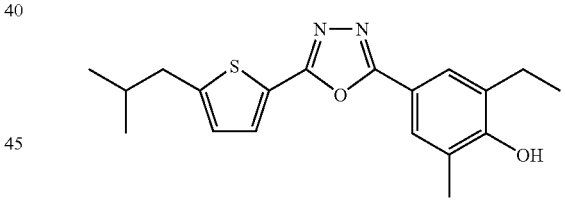

2-Ethyl-4-[5-(5-isobutyl-thiophen-2-yl)-[1,3,4]oxadiazol-2-yl]-6-methyl-phenol is prepared in analogy to Example 29 from 5-isobutyl-thiophene-2-carboxylic acid and 4-benzyloxy-3-ethyl-5-methyl-benzoic acid hydrazide; LC-MS: $t_R$=1.03 min, [M+1]$^+$=343.22.

Example 36

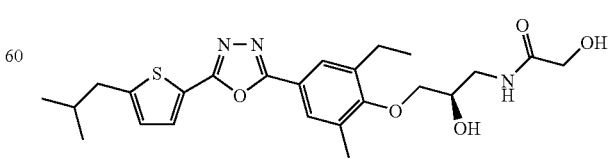

N-((2R)-3-{2-Ethyl-6-methyl-4-[5-(5-isobutyl-thiophen-2-yl)-[1,3,4]oxadiazol-2-yl]-phenoxy}-2-hydroxy-propyl)-

2-hydroxy-acetamide is prepared in analogy to Example 13 from Example 35; LC-MS: $t_R$=0.91 min, [M+1]$^+$=474.18.

Example 37

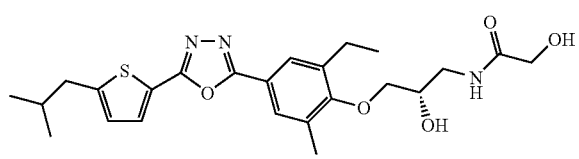

N-((2S)-3-{2-Ethyl-6-methyl-4-[5-(5-isobutyl-thiophen-2-yl)-[1,3,4]oxadiazol-2-yl]-phenoxy}-2-hydroxy-propyl)-2-hydroxy-acetamide is prepared in analogy to Example 13 from Example 35; LC-MS: $t_R$=0.91 min, [M+1]$^+$=474.17.

Example 38

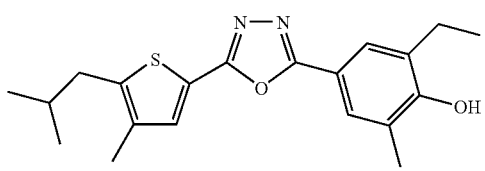

2-Ethyl-4-[5-(5-isobutyl-4-methyl-thiophen-2-yl)-[1,3,4]oxadiazol-2-yl]-6-methyl-phenol is prepared from 4-methyl-5-(2-methyl-propenyl)-thiophene-2-carboxylic acid and 4-benzyloxy-3-ethyl-5-methyl-benzoic acid hydrazide in analogy to Example 29; LC-MS: $t_R$=1.13 min, [M+1]$^+$=357.49.

Example 39

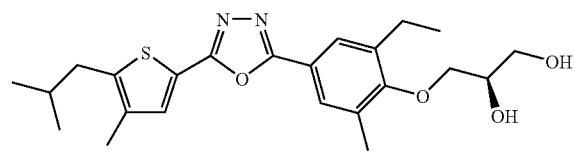

(2R)-3-{2-Ethyl-4-[5-(5-isobutyl-4-methyl-thiophen-2-yl)-[1,3,4]oxadiazol-2-yl]-6-methyl-phenoxy}-propane-1,2-diol is obtained as a white solid from Example 38 in analogy to Example 5; LC-MS: $t_R$=1.05 min; [M+1]$^+$=431.13; $^1$H NMR (CDCl$_3$): δ 1.01 (d, J=6.8 Hz, 6H), 1.31 (t, J=7.5 Hz, 3H), 1.91-2.02 (m, 1H), 2.22 (s, 3H), 2.39 (s, 3H), 2.68 (d, J=7.0 Hz, 2H), 2.75 (q, J=7.3 Hz, 2H), 3.82-3.97 (m, 4H), 4.14-4.22 (m, 1H), 7.55 (s, 1H), 7.78 (s, 1H), 7.80 (s, 1H).

Example 40

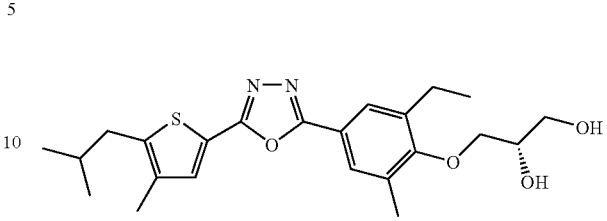

(2S)-3-{2-Ethyl-4-[5-(5-isobutyl-4-methyl-thiophen-2-yl)-[1,3,4]oxadiazol-2-yl]-6-methyl-phenoxy}-propane-1,2-diol is obtained as a white solid from Example 38 in analogy to Example 5; LC-MS: $t_R$=1.05 min, [M+1]$^+$=431.14.

Example 41

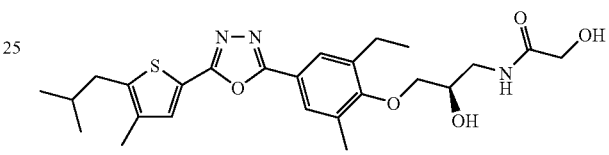

N-((2R)-3-{2-Ethyl-4-[5-(5-isobutyl-4-methyl-thiophen-2-yl)-[1,3,4]oxadiazol-2-yl]-6-methyl-phenoxy}-2-hydroxy-propyl)-2-hydroxy-acetamide is prepared from Example 38 in analogy to Example 13; LC-MS: $t_R$=1.00 min, [M+1]$^+$=488.19.

Example 42

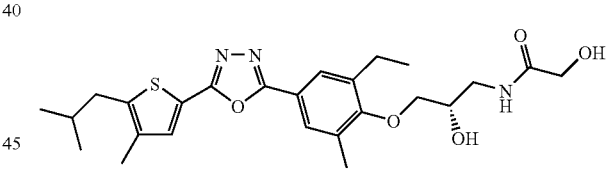

N-((2S)-3-{2-Ethyl-4-[5-(5-isobutyl-4-methyl-thiophen-2-yl)-[1,3,4]oxadiazol-2-yl]-6-methyl-phenoxy}-2-hydroxy-propyl)-2-hydroxy-acetamide is prepared from Example 38 in analogy to Example 13; LC-MS: $t_R$=1.00 min; [M+1]$^+$=488.17; $^1$H NMR δ 1.00 (d, J=6.5 Hz, 6H), 1.27 (t, J=7.5 Hz, 3H), 1.90-2.01 (m, 1H), 2.21 (s, 3H), 2.34 (s, 3H), 2.67 (d, J=7.3 Hz, 2H), 2.71 (q, J=7.5 Hz, 2H), 3.46-3.56 (m, 1H), 3.75-3.91 (m, 3H), 4.08 (s br, 2H), 4.20 (s, 3H), 7.33 (t br, J=5.5 Hz, 1H), 7.54 (s, 1H), 7.72 (s, 1H), 7.74 (s, 1H).

Example 43

GTPγS Assay to Determine EC$_{50}$ Values

GTPγS binding assays are performed in 96 well microtiter plates (Nunc, 442587) in a final volume of 200 μl, using membrane preparations of CHO cells expressing recombinant human S1P1 receptor. Assay conditions are 20 mM Hepes (Fluka, 54461), 100 mM NaCl (Fluka, 71378), 5 mM MgCl$_2$ (Fluka, 63064), 0.1% BSA (Calbiochem, 126609), 1

μM GDP (Sigma, G-7127), 2.5% DMSO (Fluka, 41644), 50 pM $^{35}$S-GTPγS (Amersham Biosciences, SJ1320). The pH is 7.4. Test compounds are dissolved and diluted in 100% DMSO and pre-incubated at room temperature for 30 min in 150 μl of the above assay buffer, in the absence of $^{35}$S-GTPγS. After addition of 50 μl of $^{35}$S-GTPγS, the assay is incubated for 1 h at rt. The assay is terminated by transfer of the reaction mixture to a Multiscreen plate (Millipore, MAHFC1H60) using a cell harvester from Packard Biosciences, and the plates are washed with ice-cold 10 mM $Na_2HPO_4/NaH_2PO_4$ (70%/30%), dried, sealed at the bottom and, after addition of 25 μl MicroScint20 (Packard Biosciences, order #6013621), sealed on the top. Membrane-bound $^{35}$S-GTPγS is measured with a TopCount from Packard Biosciences.

$EC_{50}$ is the concentration of agonist inducing 50% of the maximal specific $^{35}$S-GTPγS binding. Specific binding is determined by subtracting non-specific binding from maximal binding. Maximal binding is the amount of cpm bound to the Multiscreen plate in the presence of 10 μM of S1P. Non-specific binding is the amount of binding in the absence of an agonist in the assay.

Table 1 shows the $EC_{50}$ value of some compounds of the present invention. The $EC_{50}$ values were determined according to the method described above:

TABLE 1

| Compound of Example | $EC_{50}$ [nM] |
|---|---|
| 16 | 2.6 |
| 17 | 0.6 |
| 22 | 2.8 |
| 28 | 2.4 |
| 31 | 3.3 |
| 42 | 0.6 |

Example 44

Assessment of In Vivo Efficacy

The efficacy of the compounds of Formula (I) is assessed by measuring the circulating lymphocytes after oral administration of 3 to 30 mg/kg of a compound of Formula (I) to normotensive male Wistar rats. The animals are housed in climate-controlled conditions with a 12 h-light/dark cycle, and have free access to normal rat chow and drinking water. Blood is collected before and 3, 6 and 24 h after drug administration. Full blood is subjected to hematology using Advia Hematology system (Bayer Diagnostics, Zürich, Switzerland).

All data are presented as mean±SEM. Statistical analyses are performed by analysis of variance (ANOVA) using Statistica (StatSoft) and the Student-Newman-Keuls procedure for multiple comparisons. The null hypothesis is rejected when p<0.05.

As an example, Table 2 shows the effect on lymphocyte counts 6 h after oral administration of 10 mg/kg of some compounds of the present invention to normotensive male Wistar rats as compared to a group of animals treated with vehicle only.

TABLE 2

| Compound of Example | Lymphocyte counts |
|---|---|
| 17 | −59. ± 4% |
| 37 | −67 ± 3% |
| 40 | −58 ± 3% |

The invention claimed is:
1. A compound of the Formula (I),

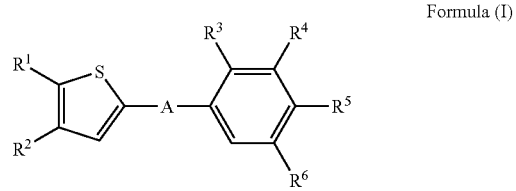

wherein
A represents *—CO—CH$_2$CH$_2$—, *—CO—CH=CH—,

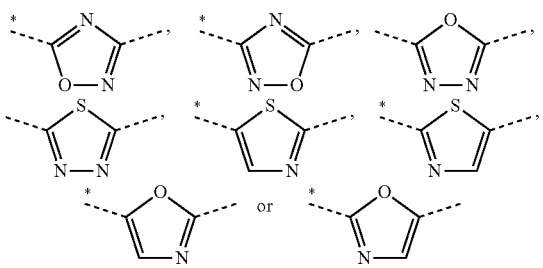

wherein the asterisks indicate the bond that is linked to the thiophene group of Formula (I);
$R^1$ represents $C_{2-5}$-alkyl;
$R^2$ represents hydrogen, methyl or ethyl;
$R^3$ represents hydrogen;
$R^4$ represents methyl, ethyl, or methoxy;
$R^5$ represents —CH$_2$—(CH$_2$)$_n$—NHSO$_2$R$^{51}$, —(CH$_2$)$_n$CH(OH)—CH$_2$—NHSO$_2$R$^{51}$, —CH$_2$—(CH$_2$)$_n$—NH-COR$^{52}$, —(CH$_2$)$_n$CH(OH)—CH$_2$—NHCOR$^{52}$, —CH$_2$—(CH$_2$)$_n$—CONR$^{53}$R$^{54}$, —CO—NHR$^{53}$, 1-(3-carboxy-azetidinyl)-2-acetyl, 1-(2-carboxy-pyrrolidinyl)-2-acetyl, 1-(3-carboxy-pyrrolidinyl)-2-acetyl, 1-(3-carboxy-azetidinyl)-3-propionyl, 1-(2-carboxy-pyrrolidinyl)-3-propionyl, 1-(3-carboxy-pyrrolidinyl)-3-propionyl, hydroxy, hydroxy-C$_{2-5}$-alkoxy, di-(hydroxy-C$_{1-4}$-alkyl)-C$_{1-4}$-alkoxy, 2,3-dihydroxypropoxy, 2-hydroxy-3-methoxy-propoxy, —OCH$_2$—(CH$_2$)$_m$—NHSO$_2$R$^{51}$, —OCH$_2$—CH(OH)—CH$_2$—NHSO$_2$R$^{51}$, —OCH$_2$—(CH$_2$)$_m$—NHCOR$^{52}$, or —OCH$_2$—CH(OH)—CH$_2$—NHCOR$^{52}$;
$R^{51}$ represents $C_{1-3}$-alkyl, methylamino, ethylamino, or dimethylamino;
$R^{52}$ represents hydroxymethyl, 2-hydroxyethyl, 2-hydroxy-1-hydroxymethyl-ethyl, or 2,3-dihydroxypropyl;
$R^{53}$ represents hydrogen, $C_{1-3}$-alkyl, 2-hydroxyethyl, 2-hydroxy-1-hydroxymethyl-ethyl, 2,3-dihydroxypropyl, carboxymethyl, 1-($C_{1-5}$-alkylcarboxy)methyl, 2-carboxyethyl, or 2-($C_{1-5}$-alkylcarboxy)ethyl;
$R^{54}$ represents hydrogen, or methyl;
m represents the integer 1 or 2;
n represents 0, 1, or 2; and
$R^6$ represents methyl, ethyl or halogen;
in free or salt form.

2. The compound according to claim 1, wherein A represents

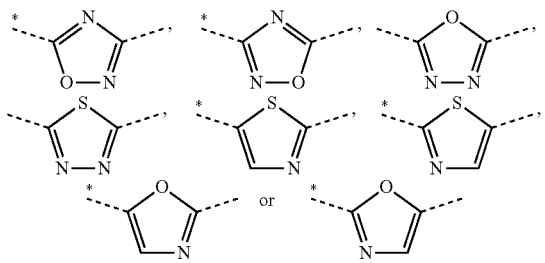

wherein the asterisks indicate the bond that is linked to the thiophene group of Formula (I), in free or salt form.

3. The compound according to claim 1, wherein A represents

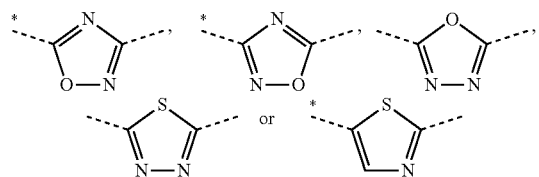

wherein the asterisks indicate the bond that is linked to the thiophene group of Formula (I), in free or salt form.

4. The compound according to claim 1, wherein A represents

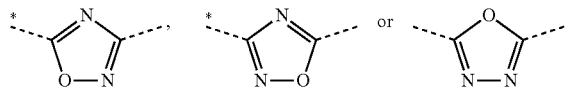

wherein the asterisks indicate the bond that is linked to the thiophene group of Formula (I), in free or salt form.

5. The compound according to claim 1, wherein A represents

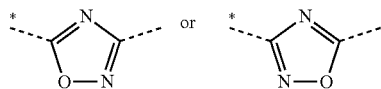

wherein the asterisks indicate the bond that is linked to the thiophene group of Formula (I), in free or salt form.

6. The compound according to claim 1, wherein A represents

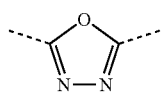

in free or salt form.

7. The compound according to claim 1, wherein $R^1$ represents n-propyl or isobutyl, in free or salt form.

8. The compound according to claim 1, wherein $R^2$ represents hydrogen or methyl, in free or salt form.

9. The compound according to claim 1, wherein $R^2$ represents hydrogen, in free or salt form.

10. The compound according to claim 1, wherein $R^3$ represents hydrogen, and $R^4$ and $R^6$ represent a methyl group, in free or salt form.

11. The compound according to claim 1, wherein $R^3$ represents hydrogen, $R^4$ represents a methyl group, and $R^6$ represents an ethyl group, in free or salt form.

12. The compound according to claim 1, wherein $R^3$ represents hydrogen, $R^4$ represents a methoxy group, and $R^6$ represents a chlorine atom, in free or salt form.

13. The compound according to claim 1, wherein $R^3$ represents hydrogen, $R^4$ represents a methyl group, and $R^6$ represents a chlorine atom, in free or salt form.

14. The compound according to claim 1, wherein $R^5$ represents —$CH_2$—$(CH_2)_n$—$NHCOR^{52}$, —$(CH_2)_n CH(OH)$—$CH_2$—$NHCOR^{52}$, hydroxy, hydroxy-$C_{2-5}$-alkoxy, di-(hydroxy-$C_{1-4}$-alkyl)-$C_{1-4}$-alkoxy, 2,3-dihydroxypropoxy, 2-hydroxy-3-methoxy-propoxy, —$OCH_2$—$(CH_2)_m$—$NHCOR^{52}$, or —$OCH_2$—$CH(OH)$—$CH_2$—$NHCOR^{52}$, in free or salt form.

15. The compound according to claim 1, wherein $R^5$ represents hydroxy, hydroxy-$C_{2-5}$-alkoxy, di-(hydroxy-$C_{1-4}$-alkyl)-$C_{1-4}$-alkoxy, 2,3-dihydroxypropoxy, 2-hydroxy-3-methoxy-propoxy, —$OCH_2$—$(CH_2)_m$—$NHCOR^{52}$, or —$OCH_2$—$CH(OH)$—$CH_2$—$NHCOR^{52}$, in free or salt form.

16. The compound according to claim 1, wherein $R^5$ represents 3-hydroxy-2-hydroxymethyl-propoxy, 2,3-dihydroxypropoxy, or —$OCH_2$—$CH(OH)$—$CH_2$—$NHCOR^{52}$, in free or salt form.

17. The compound according to claim 1, wherein $R^5$ represents 2,3-dihydroxypropoxy, or —$OCH_2$—$CH(OH)$—$CH_2$—$NHCOR^{52}$, wherein $R^{52}$ represents hydroxymethyl, in free or salt form.

18. The compound according to claim 1, wherein A represents

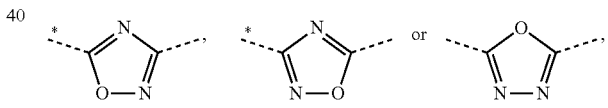

wherein the asterisks indicate the bond that is linked to the thiophene group of Formula (I); $R^1$ represents n-propyl or isobutyl; $R^2$ represents hydrogen; $R^3$ represents hydrogen; $R^4$ represents, methyl, ethyl or methoxy; $R^5$ represents 3-hydroxy-2-hydroxymethyl-propoxy, 2,3-dihydroxypropoxy, or —$OCH_2$—$CH(OH)$—$CH_2$—$NHCOR^{52}$; and $R^6$ represents methyl, ethyl or chlorine; in free or salt form.

19. The compound according to claim 1 selected from the group consisting of (2R)—N-(3-{4-[5-(5-ethyl-thiophen-2-yl)-[1,2,4]oxadiazol-3-yl]-2,6-dimethyl-phenoxy}-2-hydroxy-propyl)-2-hydroxy-acetamide, (2S)—N-(3-{4-[5-(5-ethyl-thiophen-2-yl)-[1,2,4]oxadiazol-3-yl]-2,6-dimethyl-phenoxy}-2-hydroxy-propyl)-2-hydroxy-acetamide, (2R)—N-(3-{2,6-dimethyl-4-[5-(5-butyl-thiophen-2-yl)-[1,2,4]oxadiazol-3-yl]-phenoxy}-2-hydroxy-propyl)-2-hydroxy-acetamide, (2S)—N-(3-{2,6-dimethyl-4-[5-(5-butyl-thiophen-2-yl)-[1,2,4]oxadiazol-3-yl]-phenoxy}-2-hydroxy-propyl)-2-hydroxy-acetamide, (2R)—N-(3-{2,6-dimethyl-4-[5-(5-isobutyl-thiophen-2-yl)-[1,2,4]oxadiazol-3-yl]-phenoxy}-2-hydroxy-propyl)-2-hydroxy-acetamide,
(2S)—N-(3-{2,6-dimethyl-4-[5-(5-isobutyl-thiophen-2-yl)-[1,2,4]oxadiazol-3-yl]-phenoxy}-2-hydroxy-propyl)-2-hydroxy-acetamide,
(2R)—N-(3-{2-ethyl-6-methyl-4-[5-(5-isobutyl-thiophen-2-yl)-[1,2,4]oxadiazol-3-yl]-phenoxy}-2-hydroxy-propyl)-2-hydroxy-acetamide,
(2S)—N-(3-{2-ethyl-6-methyl-4-[5-(5-isobutyl-thiophen-2-yl)-[1,2,4]oxadiazol-3-yl]-phenoxy}-2-hydroxy-propyl)-2-hydroxy-acetamide,
(2R)—N-(3-{2,6-dimethyl-4-[5-(5-propyl-thiophen-2-yl)-[1,2,4]oxadiazol-3-yl]-phenoxy}-2-hydroxy-propyl)-2-hydroxy-acetamide,
(2S)—N-(3-{2,6-dimethyl-4-[5-(5-propyl-thiophen-2-yl)-[1,2,4]oxadiazol-3-yl]-phenoxy}-2-hydroxy-propyl)-2-hydroxy-acetamide,
(2R)—N-(3-{2-ethyl-6-methyl-4-[5-(5-propyl-thiophen-2-yl)-[1,2,4]oxadiazol-3-yl]-phenoxy}-2-hydroxy-propyl)-2-hydroxy-acetamide,
(2S)—N-(3-{2-ethyl-6-methyl-4-[5-(5-propyl-thiophen-2-yl)-[1,2,4]oxadiazol-3-yl]-phenoxy}-2-hydroxy-propyl)-2-hydroxy-acetamide,
(2R)—N-(3-{2-ethyl-4-[5-(5-isobutyl-thiophen-2-yl)-[1,2,4]oxadiazol-3-yl]-6-methyl-phenoxy}-2-hydroxy-propyl)-2-hydroxy-acetamide,
(2S)—N-(3-{2-ethyl-4-[5-(5-isobutyl-thiophen-2-yl)-[1,2,4]oxadiazol-3-yl]-6-methyl-phenoxy}-2-hydroxy-propyl)-2-hydroxy-acetamide,
(2R)-3-{4-[5-(5-isobutyl-thiophen-2-yl)-[1,3,4]oxadiazol-2-yl]-2,6-dimethyl-phenoxy}-propane-1,2-diol,
(2S)-3-{4-[5-(5-isobutyl-thiophen-2-yl)-[1,3,4]oxadiazol-2-yl]-2,6-dimethyl-phenoxy}-propane-1,2-diol,
(2R)-2-hydroxy-N-(2-hydroxy-3-{4-[5-(5-isobutyl-thiophen-2-yl)-[1,3,4]oxadiazol-2-yl]-2,6-dimethyl-phenoxy}-propyl)-acetamide,
(2S)-2-hydroxy-N-(2-hydroxy-3-{4-[5-(5-isobutyl-thiophen-2-yl)-[1,3,4]oxadiazol-2-yl]-2,6-dimethyl-phenoxy}-propyl)-acetamide,
(2R)-2-hydroxy-N-(2-hydroxy-3-{4-[5-(5-isobutyl-thiophen-2-yl)-[1,3,4]oxadiazol-2-yl]-2-ethyl-6-methyl-phenoxy}-propyl)-acetamide, and
(2S)-2-hydroxy-N-(2-hydroxy-3-{4-[5-(5-isobutyl-thiophen-2-yl)-[1,3,4]oxadiazol-2-yl]-2-ethyl-6-methyl-phenoxy}-propyl)-acetamide,
in free or salt form.

20. The compound according to claim 1 selected from the group consisting of:
2-hydroxy-N-((2S)-2-hydroxy-3-{4-[5-(5-isobutyl-thiophen-2-yl)-[1,3,4]oxadiazol-2-yl]-2,6-dimethyl-phenoxy}-propyl)-acetamide,
N-((2S)-3-{2-ethyl-6-methyl-4-[5-(5-propyl-thiophen-2-yl)-[1,3,4]oxadiazol-2-yl]-phenoxy}-2-hydroxy-propyl)-2-hydroxy-acetamide,
(2R)-3-{2-ethyl-4-[5-(5-isobutyl-4-methyl-thiophen-2-yl)-[1,3,4]oxadiazol-2-yl]-6-methyl-phenoxy}-propane-1,2-diol,
(2S)-3-{2-ethyl-4-[5-(5-isobutyl-4-methyl-thiophen-2-yl)-[1,3,4]oxadiazol-2-yl]-6-methyl-phenoxy}-propane-1,2-diol,
N-((2R)-3-{2-ethyl-4-[5-(5-isobutyl-4-methyl-thiophen-2-yl)-[1,3,4]oxadiazol-2-yl]-6-methyl-phenoxy}-2-hydroxy-propyl)-2-hydroxy-acetamide, and
N-((2S)-3-{2-ethyl-4-[5-(5-isobutyl-4-methyl-thiophen-2-yl)-[1,3,4]oxadiazol-2-yl]-6-methyl-phenoxy}-2-hydroxy-propyl)-2-hydroxy-acetamide,
in free or salt form.

21. A pharmaceutical composition comprising a compound according to claim 1, in free or pharmaceutically acceptable salt form, and a pharmaceutically acceptable carrier.

* * * * *